United States Patent
Nakamine et al.

(10) Patent No.: US 6,649,771 B2
(45) Date of Patent: Nov. 18, 2003

(54) SILVER HALIDE COLOR PHOTOGRAPHIC LIGHT-SENSITIVE MATERIAL, PYRROLOTRIAZOLE COMPOUND AND DYE-FORMING COMPOUND

(75) Inventors: Takeshi Nakamine, Minami-ashigara (JP); Nobuo Seto, Minami-ashigara (JP); Hideaki Sato, Minami-ashigara (JP); Yasuaki Deguchi, Minami-ashigara (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/816,246

(22) Filed: Mar. 26, 2001

(65) Prior Publication Data

US 2002/0031736 A1 Mar. 14, 2002

(30) Foreign Application Priority Data

Mar. 27, 2000 (JP) .......................... 2000-87451
Jul. 21, 2000 (JP) ........................ 2000-221434

(51) Int. Cl.⁷ ..................... C07D 487/04; G03C 1/49
(52) U.S. Cl. .................. 548/262.4; 544/58.4; 544/144; 544/366; 546/187; 430/558
(58) Field of Search ....... 548/262.4; 544/58.4, 544/144, 366; 546/187; 430/558

(56) References Cited

U.S. PATENT DOCUMENTS 6,132,945 A * 10/2000 Saito et al. ................. 430/546
6,220,925 B1 * 4/2001 Saito et al. ................. 450/546

FOREIGN PATENT DOCUMENTS

| EP | 0 491 197 A1 | 6/1992 | .......... G03C/7/38 |
| EP | 0 545 300 A1 | 6/1993 | .......... G03C/7/38 |
| EP | 0 628 867 A1 | 12/1994 | .......... G03C/7/38 |
| EP | 10198009 | 7/1998 | |
| EP | 0 883 024 A1 * | 12/1998 | |
| EP | 0 894 786 A1 | 3/1999 | |
| JP | 9-189988 | 7/1997 | .......... G03C/7/38 |
| JP | 10-198012 | 7/1998 | .......... G03C/7/38 |

* cited by examiner

Primary Examiner—Joseph K. McKane
Assistant Examiner—Rebecca Anderson
(74) Attorney, Agent, or Firm—Sughrue Mion, PLLC

(57) ABSTRACT

A pyrrolotriazole compound of the following formula (I), and a silver halide color photographic light-sensitive material containing the pyrrolotriazole compound as a cyan coupler:

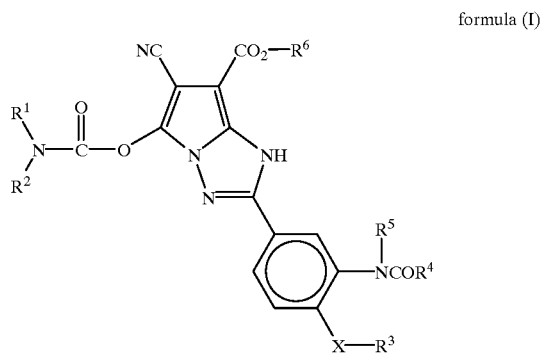

formula (I)

wherein $R^1$ and $R^2$ each independently are an alkyl, cycloalkyl, alkenyl, aryl or heterocyclic group, provided that $R^1$ and $R^2$ may bond together to form a 5- or 6-membered nitrogen-containing heterocycle; $R^3$ is an alkyl, cycloalkyl, alkenyl, aryl or heterocyclic group; $R^4$ is an alkyl, cycloalkyl, alkenyl, alkoxy or amino group; $R^5$ is a hydrogen atom, an alkyl or aryl group; $R^6$ is an alkyl, cycloalkyl or alkenyl group; and X is an oxygen or sulfur atom.

16 Claims, No Drawings

SILVER HALIDE COLOR PHOTOGRAPHIC LIGHT-SENSITIVE MATERIAL, PYRROLOTRIAZOLE COMPOUND AND DYE-FORMING COMPOUND

FIELD OF THE INVENTION

The present invention relates to a silver halide color photographic light-sensitive material containing a novel cyan coupler. The present invention also relates to a novel pyrrolotriazole compound and a dye-forming compound.

BACKGROUND OF THE INVENTION

It is well known that, in a silver halide color photographic light-sensitive material, an aromatic primary amine color-developing agent, oxidized by an exposed silver halide, which is an oxidizing agent, reacts with a coupler, to form a dye, such as indophenols, indoanilines, indamines, azomethines phenoxazines, and phenazines, thereby forming a dye image. This photography system employs subtractive color photography, and a dye image is formed by yellow, magenta, and cyan dyes. Hitherto, in order to form a cyan dye image, among the above dyes, phenol or naphthol couplers have generally been used. However, these couplers have the serious problem that dyes derived from these couplers have undesirable absorption in the green region, which results in deterioration of color reproduction. Accordingly, it is strongly desired to resolve this problem.

As a means for resolving this problem, use of the heterocyclic compounds described in, for example, U.S. Pat. Nos. 4,728,598 and 4,873,183, and European Patent No. 249453 A2, is proposed. However, these couplers have such fatal problems as low coupling activity. As a coupler that has overcome these problems, pyrroloazole couplers, described in, for example, European Patent Nos. 0491197 A1, 0488248, 0545300, 0628867 A1, and 0484909; U.S. Pat. No. 5,164,289, and JP-A-6-347960 ("JP-A" means unexamined published Japanese patent application), are proposed. These couplers are excellent in both hue of the resulting dye and coupling activity. Further, they are also excellent in that the molecular extinction coefficient of the resulting dye is high.

However, there is a problem that dyes derived from these pyrroloazole couplers are apt to cause aggregation in a film, which results in a difference in hue between a high-density portion and a low-density portion. This problem is particularly conspicuously when the amount of a high-boiling-point organic solvent (oil) to be used in emulsifying is small.

As a means of resolving this problem, JP-A-9-189988 and JP-A-10-198012 disclose pyrroloazole couplers. Although the dye image resulting from these pyrroloazole couplers is indeed excellent in hue, color reproduction of the green-to-blue color range is not yet satisfactory. That is, since the extinction coefficient in the magenta region, which is not wanted for the cyan dye image, is large, there is dissatisfaction, as the current strong demand is for a picture that has improved color reproduction.

Further, the dye image resulting from these pyrroloazole couplers is not satisfactory in terms of light resistance, so that further improvement has been demanded.

On the other hand, in addition to the foregoing silver halide color photographic light-sensitive material, development of compounds capable of providing excellent hue and light resistance as mentioned above, especially dye-forming compounds, is strongly demanded in such an art, in which especially use is made of a dye for the image.

SUMMARY OF THE INVENTION

The present invention is a silver halide color photographic light-sensitive material which comprises a cyan coupler represented by the following formula (I):

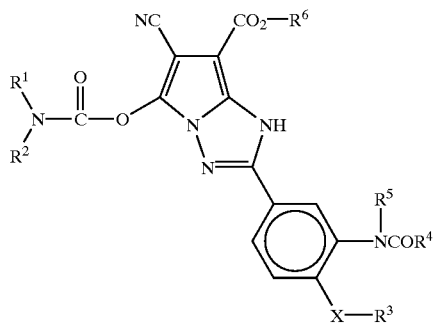

formula (I)

wherein $R^1$ and $R^2$ each independently represent an alkyl group, a cycloalkyl group, an alkenyl group, an aryl group, or a heterocyclic group, provided that $R^1$ and $R^2$ may combine with each other to form a 5- or 6-membered nitrogen-containing heterocycle; $R^3$ represents an alkyl group, a cycloalkyl group, an alkenyl group, an aryl group, or a heterocyclic group; $R^4$ represents an alkyl group, a cycloalkyl group, an alkenyl group, an alkoxy group, or an amino group; $R^5$ represents a hydrogen atom, an alkyl group, or an aryl group; $R^6$ represents an alkyl group, a cycloalkyl group, or an alkenyl group; and X represents an oxygen atom, or a sulfur atom.

Further, the present invention is a pyrrolotriazole compound represented by the above formula (I).

Still further, the present invention is a dye-forming compound represented by the above formula (I).

Other and further features and advantages of the invention will appear more fully from the following description.

DETAILED DESCRIPTION OF THE INVENTION

The present inventors have found a novel pyrrolotriazole compound which can be used as a dye-forming compound.

According to the present invention, there are provided the following means:

(1) A silver halide color photographic light-sensitive material comprising a cyan coupler represented by the following formula (I):

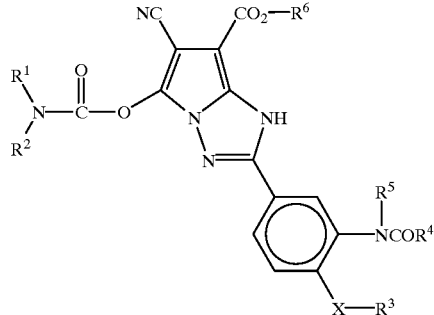

formula (I)

wherein $R^1$ and $R^2$ each independently represent an alkyl group, a cycloalkyl group, an alkenyl group, an aryl group, or a heterocyclic group, provided that $R^1$ and $R^2$ may combine with each other to form a 5- or 6-membered nitrogen-containing heterocycle; $R^3$ represents an alkyl group, a cycloalkyl group, an alkenyl group, an aryl group, or a heterocyclic group; $R^4$ represents an alkyl group, a cycloalkyl group, an alkenyl group, an alkoxy group, or an amino group; $R^5$ represents a hydrogen atom, an alkyl group, or an aryl group; $R^6$ represents an alkyl group, a cycloalkyl group, or an alkenyl group; and X represents an oxygen atom, or a sulfur atom;

(2) A pyrrolotriazole compound represented by the following formula (I):

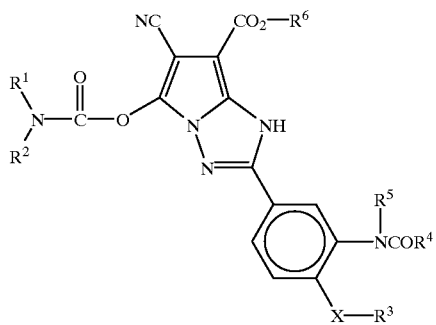

formula (I)

wherein $R^1$ and $R^2$ each independently represent an alkyl group, a cycloalkyl group, an alkenyl group, an aryl group, or a heterocyclic group, provided that $R^1$ and $R^2$ may combine with each other to form a 5- or 6-membered nitrogen-containing heterocycle; $R^3$ represents an alkyl group, a cycloalkyl group, an alkenyl group, an aryl group, or a heterocyclic group; $R^4$ represents an alkyl group, a cycloalkyl group, an alkenyl group, an alkoxy group, or an amino group; $R^5$ represents a hydrogen atom, an alkyl group, or an aryl group; $R^6$ represents an alkyl group, a cycloalkyl group, or an alkenyl group; and X represents an oxygen atom, or a sulfur atom; and (3) A dye-forming compound represented by the following formula (I):

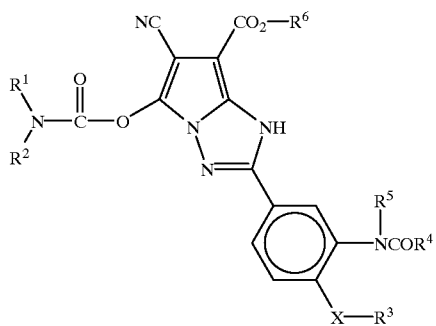

formula (I)

wherein $R^1$ and $R^2$ each independently represent an alkyl group, a cycloalkyl group, an alkenyl group, an aryl group, or a heterocyclic group, provided that $R^1$ and $R^2$ may combine with each other to form a 5- or 6-membered nitrogen-containing heterocycle; $R^3$ represents an alkyl group, a cycloalkyl group, an alkenyl group, an aryl group, or a heterocyclic group; $R^4$ represents an alkyl group, a cycloalkyl group, an alkenyl group, an alkoxy group, or an amino group; $R^5$ represents a hydrogen atom, an alkyl group, or an aryl group; $R^6$ represents an alkyl group, a cycloalkyl group, or an alkenyl group; and X represents an oxygen atom, or a sulfur atom.

The present invention will be described in detail below.

As to the substituent for use in the present invention, the substituent including a group of substituents described below is defined as the term "$R^{40}$" in this specification.

Namely, examples of the above-described group of substituents include a halogen atom (e.g., fluorine, chlorine, bromine), an alkyl group (preferably a straight or branched chain alkyl group having 1 to 40 carbon atoms, e.g., methyl, ethyl, propyl, isopropyl, butyl, t-butyl, 1-octyl, tridecyl), a cycloalkyl group (preferably a cycloalkyl group having 3 to 40 carbon atoms, e.g., cyclopropyl, 1-ethylcyclopropyl, cyclopentyl, cyclohexyl, 1-norbornyl, 1-adamantyl), an alkenyl group (preferably an alkenyl group having 2 to 40 carbon atoms, e.g., vinyl, allyl, 3-butene-1-yl), an aryl group (preferably an aryl group having 6 to 32 carbon atoms, e.g., phenyl, 1-naphthyl, 2-naphthyl), a heterocyclic group (preferably a 5- to 8-membered heterocyclic group having 1 to 32 carbon atoms, more preferably having at least one ring-constituting atom selected from the group of nitrogen, oxygen and sulfur, e.g., 2-thienyl, 4-pyridyl, 2-furyl, 2-pyrimidinyl, 1-pyridyl, 2-benzothiazolyl, 1-imidazolyl, 1-pyrazolyl, benzotriazole-2-yl), a cyano group, a silyl group (preferably a ilyl group having 3 to 40 carbon atoms, e.g., trimethylsilyl, triethylsilyl, tributylsilyl, t-butyldimethylsilyl, t-hexyldimethylsilyl), a hydroxyl group, a carboxyl group, a nitro group, an alkoxy group (preferably an alkoxyl group having 1 to 40 carbon atoms, e.g., methoxy, ethoxy, 1-butoxy, 2-butoxy, isopropoxy, t-butoxy, dodecyloxy), a cycloalkyloxy group (preferably a cycloalkyloxy group having 3 to 8 carbon atoms, e.g., cyclopentyloxy, cyclohexyloxy), an aryloxy group (preferably an aryloxy group having 6 to 40 carbon atoms, e.g., phenoxy, 2-naphthoxy), a herocyclic oxy group (preferably a heterocyclic oxy group having 1 to 40 carbon atoms, more preferably having the same heterocycle moiety that is described in the above heterocyclic group, e.g., 1-phenyltetrazole-5-oxy, 2-tetrahydropyranyloxy, 2-furyloxy), a silyloxy group (preferably a silyloxy group having 1 to 40 carbon atoms, e.g., trimethylsilyloxy, t-butyldimethylsilyloxy, diphenylmethylsilyloxy), an acyloxy group (preferably an acyloxy group having 2 to 40 carbon atoms, e.g., acetoxy, pivaloyloxy, benzoyloxy, dodecanoyloxy), an alkoxycarbonyloxy group (preferably an alkoxycarbonyloxy group having 2 to 40 carbon atoms, e.g., ethoxycarbonyloxy, t-butoxycarbonyloxy), a cycloalkyloxycarbonyloxy group (preferably a cycloalkyloxycarbonyloxy group having 4 to 40 carbon atoms, e.g., cyclohexyloxycarbonyloxy), an aryloxycarbonyloxy group (preferably an aryloxycarbonyloxy group having 7 to 40 carbon atoms, e.g., phenoxycarbonyloxy), a carbamoyloxy group (preferably a carbamoyloxy group having 1 to 40 carbon atoms, e.g., N,N-dimethylcarbamoyloxy, N-butylcarbamoyloxy), a sulfamoyloxy group (preferably a sulfamoyloxy group having 1 to 40 carbon atoms, e.g., N,N-diethylsulfamoyloxy, N-propylsulfamoyloxy), an alkanesulfonyloxy group (preferably an alkanesulfonyloxy group having 1 to 40 carbon atoms, e.g., methanesulfonyloxy, hexadecanesulfonyloxy), an arylsulfonyloxy group (preferably an arylsulfonyloxy group having 6 to 40 carbon atoms, e.g., benzenesulfonyloxy), an acyl group (preferably an acyl group having 1 to 40 carbon atoms, e.g., formyl, acetyl, pivaloyl, benzoyl, tetradecanoyl), an alkoxycarbonyl group (preferably an alkoxycarbonyl group having 2 to 40 carbon atoms, e.g., methoxycarbonyl, ethoxycarbonyl, octadecyloxycarbonyl), a cycloalkyloxycarbonyl group (preferably a cycloalkyloxycarbonyl group having 4 to 40 carbon atoms, e.g., cyclohexyloxycarbonyl), an aryloxycarbonyl group (preferably an aryloxycarbonyl group having 7 to 40 carbon atoms, e.g., phenoxycarbonyl), a carbamoyl group (preferably a carbamoyl group having 1 to 40 carbon atoms, e.g., carbamoyl, N,N-dibutylcarbamoyl, N-ethyl-N-octylcarbamoyl, N-propylcarbamoyl), an amino group {an unsubstituted amino group, an alkylamino group, an anilino group and a heterocyclic amino group are included, for example, an unsubstituted amino group, an alkylamino group (preferably an alkylamino group having 1 to 32 carbon atoms, e.g., methylamino, N,N-dioctylamino, tetradecylamino, octadecyl amino), an anilino group (preferably an anilino group having 6 to 40 carbon atoms, e.g., anilino, N-methylanilino), a heterocyclic amino group (preferably a heterocyclic amino group having 1 to 40 carbon atoms, more preferably having the same heterocyclic moiety as described in the above-described heterocyclic group, e.g., 4-pyridylamino)}, a carbonamido group (preferably a carbonamido group having 2 to 40 carbon atoms, e.g., acetoamido, benzamido, tetradecaneamido), a ureido group (preferably a ureido group having 1 to 40 carbon atoms, e.g., ureido, N,N-dimethylureido, N-phenylureido), an imido group (preferably an imido group having 10 or less carbon atoms, e.g., N-succinimido, N-phthalimido), an alkoxycarbonylamino group (preferably an alkoxycarbonylamino group having 2 to 40 carbon atoms, e.g., methoxycarbonylamino, ethoxycarbonylamino, t-butoxycarbonylamino, octadecyloxycarbonylamino), a cycloalkyloxycarbonylamino group (preferably a cycloalkyloxycarbonylamino group having 4 to 40 carbon atoms, e.g., cyclohexyloxycarbonylamino), an aryloxycarbonylamino group (preferably an aryloxycarbonylamino group having 7 to 40 carbon atoms, e.g., phenoxycarbonylamino), a sulfonamido group (preferably a sulfonamido group having 1 to 40 carbon atoms, e.g., methanesulfonamido, butanesulfonamido, benzenesulfonamido, hexadecanesulfonamido), a sulfamoylamino group (preferably a sulfamoylamino group having 1 to 40 carbon atoms e.g., N,N-dipropylsulfamoylamino, N-ethyl-N-dodecylsulfamoylamino), an azo group (preferably an azo group having 1 to 40 carbon atoms e.g., phenylazo), an alkylthio group (preferably an alkylthio group having 1 to 40 carbon atoms e.g., ethylthio, octylthio), a cycloalkylthio group (preferably a cycloalkylthio group having 3 to 40 carbon atoms e.g., cyclohexylthio), an arylthio group (preferably an arylthio group having 6 to 40 carbon atoms, e.g., phenylthio), a heterocyclic thio group (preferably a heterocyclic thio group having 1 to 40 carbon atoms wherein the heterocyclic moiety is the same as that described for the above-described heterocyclic group, e.g., 2-benzothiazolylthio, 2-pyridylthio, 1-phenyltetrazolylthio), an alkylsulfinyl group (preferably an alkylsulfinyl group having 1 to 40 carbon atoms, e.g., dodecanesulfinyl), an arylsulfinyl group (preferably an arylsulfinyl group having 6 to 40 carbon atoms, e.g., benzenesulfinyl), an alkanesulfonyl group (preferably an alkanesulfonyl group having 1 to 40 carbon atoms, e.g., methanesulfonyl, octanesulfonyl), an arylsulfonyl group (preferably an arylsulfonyl group having 6 to 40 carbon atoms, e.g., benzenesulfonyl, 1-naphthalenesulfonyl), an alkoxysulfonyl group (preferably an alkoxysulfonyl group having 1 to 40 carbon atoms, e.g., methoxysulfonyl, ethoxysulfonyl), a cycloalkyloxysulfonyl group (preferably a cycloalkyloxysulfonyl group having 3 to 40 carbon atoms, e.g., cyclopropyloxysulfonyl), an aryloxysulfonyl group (preferably an aryloxysulfonyl group having 6 to 40 carbon atoms, e.g., phenoxysulfonyl, p-methylphenoxysulfonyl), a sulfamoyl group (preferably a sulfamoyl group having 32 or less carbon atoms, e.g., sulfamoyl, N,N-dipropylsulfamoyl, N-ethyl-N-dodecylsulfamoyl), a sulfo group, a phosphonyl group (preferably a phosphonyl group having 1 to 40 carbon atoms, e.g., phenoxyphosphonyl, octyloxyphosphonyl, phenylphosphonyl), and a phosphinoylamino group (preferably a phosphinoylamino group having 2 to 40 carbon atoms, e.g., diethoxyphosphinoylamino, dioctyloxyphosphinoylamino).

The compounds, represented by the above formula (I), of the present invention will be explained below.

In the foregoing formula (I), $R^1$ and $R^2$ each independently represent an alkyl group, a cycloalkyl group, an alkenyl group, an aryl group, or a heterocyclic group. Preferable specific examples of these groups are the same as those of the alkyl, cycloalkyl, alkenyl, aryl group and heterocyclic groups, which are previously exemplified for the above-mentioned $R^{40}$. $R^1$ and $R^2$ may be the same or different from each other. $R^1$ and $R^2$ may have a substituent. Examples of the substituent are the same as those exemplified in the above-mentioned $R^{40}$. $R^1$ and $R^2$ may combine with each other to form a 5- or 6-membered nitrogen-containing heterocycle. The nitrogen-containing heterocycle may be a saturated, unsaturated or aromatic heterocycle. The ring-constituting atom of the above heterocycle is preferably selected from a group consisting of carbon, nitrogen, oxygen and sulfur atoms. Specific examples of the heterocyclic group include 1-pyrrolidinyl, 1-piperidinyl, morpholino, 2-oxymorpholino, thiomorpholino, 1,1-dioxothiomorpholino, piperadinyl, 1-pyrrolyl, indolyl, pyrazolidinyl, 1,4-dihydropyridine-1-yl, 2-oxymorpholino, 3-thiazolidine and 3-pyrroline-1-yl.

The above-mentioned nitrogen-containing heterocycle may have a substituent. Examples of the substituent are the same as those exemplified in the above-mentioned $R^{40}$.

Each of $R^1$ and $R^2$ is preferably an alkyl group, a cycloalkyl group, or an alkenyl group. In this case, the carbon number of these groups is preferably in the range of 1 to 10, more preferably in the range of 1 to 5.

Further, it is also preferable that $R^1$ and $R^2$ bond together, to form a nitrogen-containing heterocycle.

Preferable specific examples of the group represented by $R^1R^2N$—, which is a partial structure of the formula (I), are shown below. However, the present invention is not limited thereto.

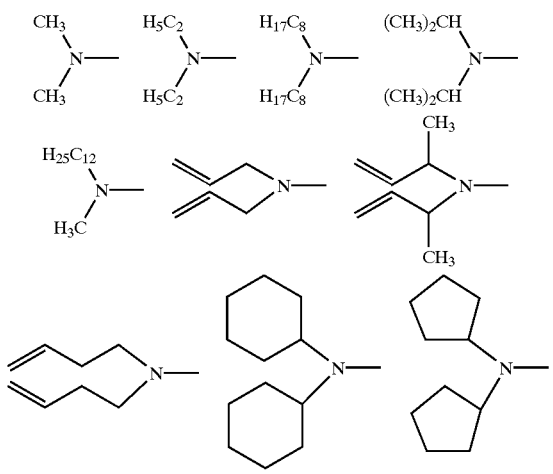

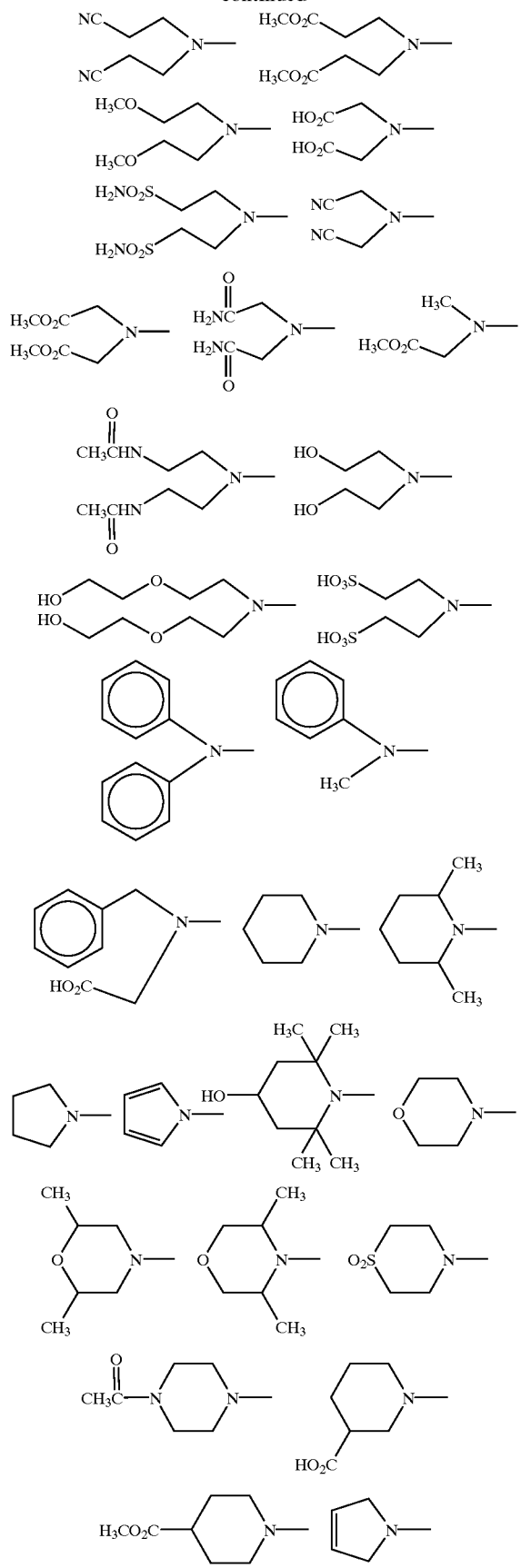

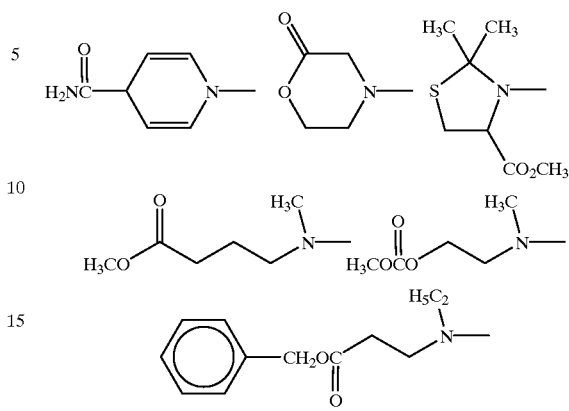

$R^3$ represents an alkyl group, a cycloalkyl group, an alkenyl group, an aryl group, or a heterocyclic group. Preferable specific examples of these groups are the same as those of the alkyl, cycloalkyl, alkenyl, aryl and heterocyclic groups, which are previously exemplified in the above-mentioned $R^{40}$.

$R^3$ may have a substituent. Examples of the substituent are the same as those exemplified in the above-mentioned $R^{40}$.

$R^3$ is preferably an alkyl group, a cycloalkyl group or an aryl group, and it is most preferably a substituted or unsubstituted alkyl group. The carbon number of $R^3$ is preferably in the range of 1 to 10, more preferably in the range of 1 to 3.

$R^4$ represents an alkyl group, a cycloalkyl group, an alkenyl group, an alkoxy group, or an amino group. Preferable specific examples of these groups are the same as those of the alkyl, cycloalkyl, alkenyl, alkoxy and amino groups, which are previously exemplified in the above-mentioned $R^{40}$.

$R^4$ is preferably an alkyl group, or a cycloalkyl group. The carbon number of these groups is preferably in the range of 1 to 20, more preferably in the range of 1 to 10, and furthermore preferably in the range of 1 to 5.

Further, $R^4$ is preferably a branched alkyl, or cycloalkyl group, more preferably a secondary or tertiary alkyl or cycloalkyl group, furthermore preferably a tertiary alkyl group, and most preferably a tertiary unsubstituted alkyl group.

$R^5$ represents a hydrogen atom, an alkyl group, or an aryl group. When $R^5$ represents an alkyl group, or an aryl group, preferable specific examples of these groups are the same as those of the alkyl and aryl groups, which are previously exemplified in the above-mentioned $R^{40}$.

$R^5$ may have a substituent. Examples of the substituent are the same as those exemplified in the above-mentioned $R^{40}$.

$R^5$ is preferably a hydrogen atom or an alkyl group. When $R^5$ represents an alkyl group, the carbon number of the group is preferably in the range of 1 to 10, more preferably in the range of 1 to 5. Most preferably $R^5$ is a hydrogen atom.

$R^6$ represents an alkyl group, a cycloalkyl group, or an alkenyl group. Preferable specific examples of these groups are the same as those of the alkyl, cycloalkyl, and alkenyl groups, which are previously exemplified in the above-mentioned $R^{40}$. $R^6$ may have a substituent. Examples of the substituent are the same as those exemplified in the above-mentioned $R^{40}$.

Preferably $R^6$ is a group represented by the following formula (II):

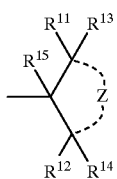

formula (II)

In formula (II), $R^{11}$ and $R^{12}$ each independently represent an alkyl group, a cycloalkyl group, or an alkenyl group. Preferable specific examples of these groups are the same as those of the alkyl, cycloalkyl, and alkenyl groups, which are previously exemplified in the above-mentioned $R^{40}$. $R^{13}$, $R^{14}$ and $R^{15}$ each independently represent a hydrogen atom, an alkyl group, a cycloalkyl group, or an alkenyl group. When $R^{13}$, $R^{14}$ and $R^{15}$ each represent an alkyl group, a cycloalkyl group, or an alkenyl group, preferable specific examples of these groups are the same as those of the alkyl, cycloalkyl and alkenyl groups, which are previously exemplified in the above-mentioned $R^{40}$. Preferably $R^{13}$, $R^{14}$ and $R^{15}$ each represent a hydrogen atom.

Z represents carbon atoms necessary to form a 5- to 8-membered ring, which ring may be substituted, and which ring may be a saturated ring or an unsaturated ring. When the ring has a substituent, examples of the substituent are the same as those exemplified in the above-mentioned $R^{40}$.

Examples of the ring which is formed together with Z include cyclopentane, cyclohexane, cycloheptane, cyclooctane and cyclohexene rings. The ring which is formed with Z is preferably a 5- or 6-membered ring, more preferably a cyclohexane ring which may have a substituent.

X represents an oxygen atom, or a sulfur atom. Preferably X represents an oxygen atom.

Specific examples of the compound represented by formula (I) of the present invention are shown below. However, the present invention is not limited thereto.

(1)

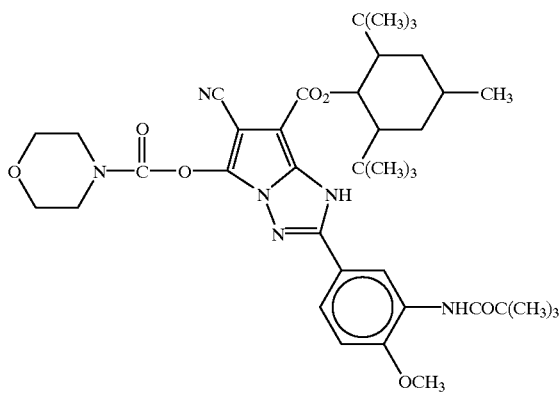

(2)

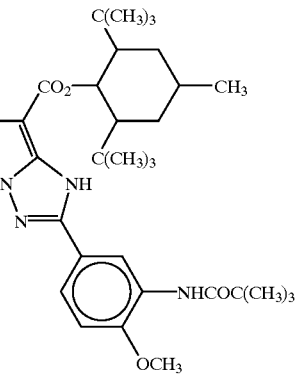

(3)

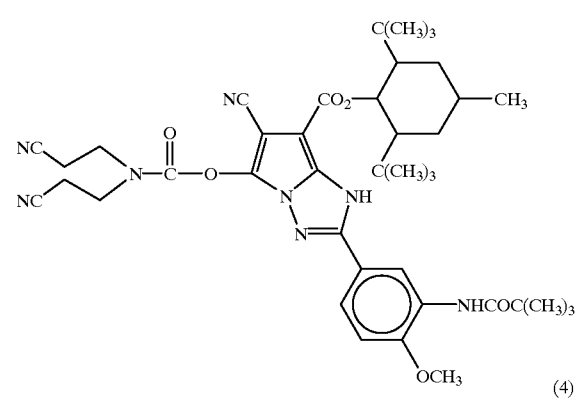

(4)

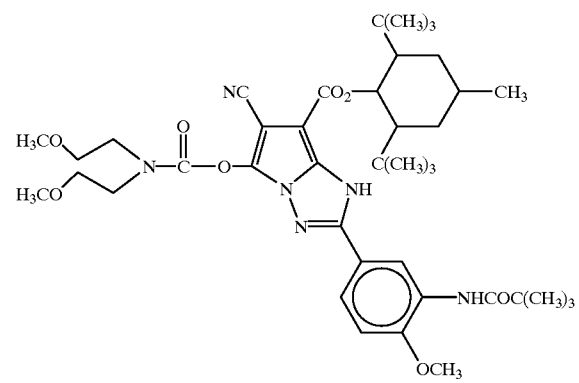

(5)

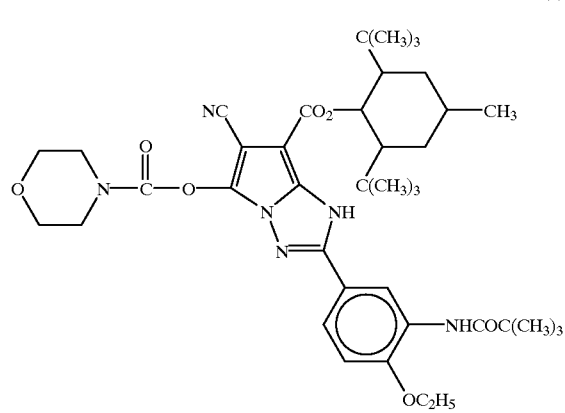

-continued
(6)
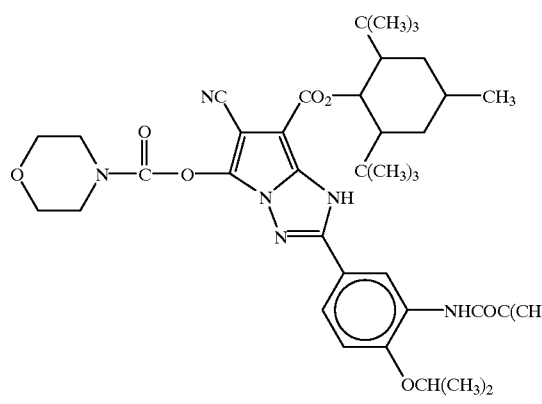
(7)
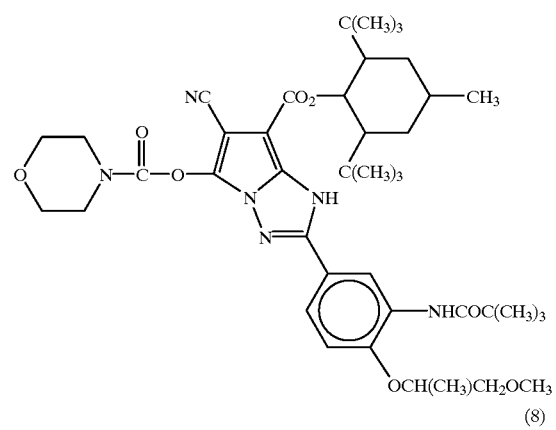
(8)
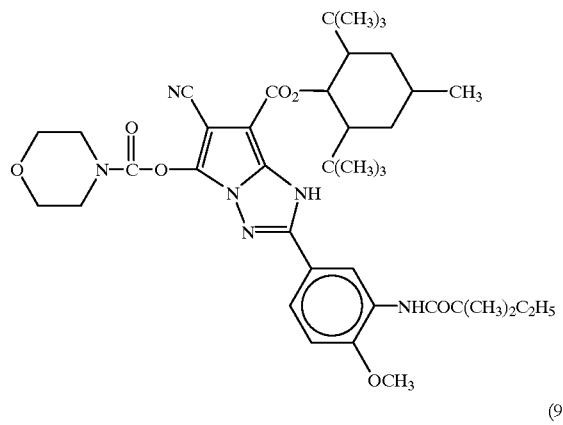
(9)
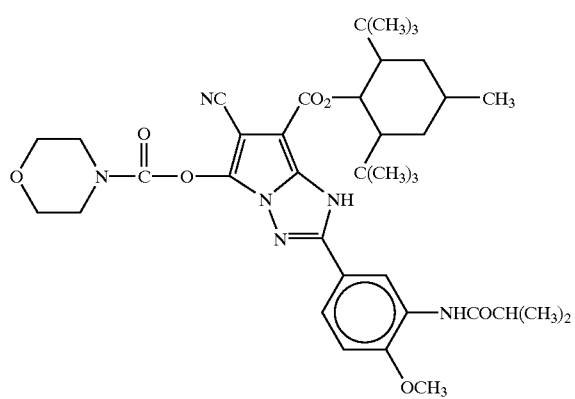
-continued
(10)
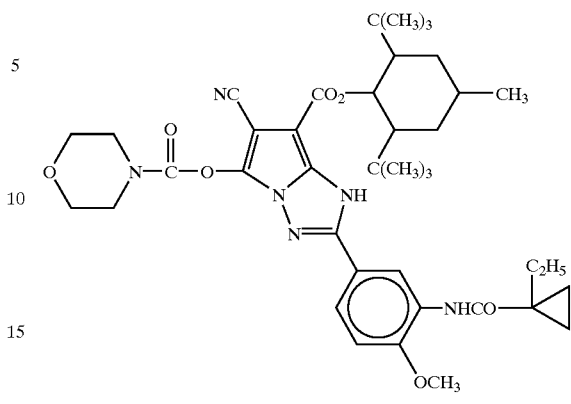
(11)
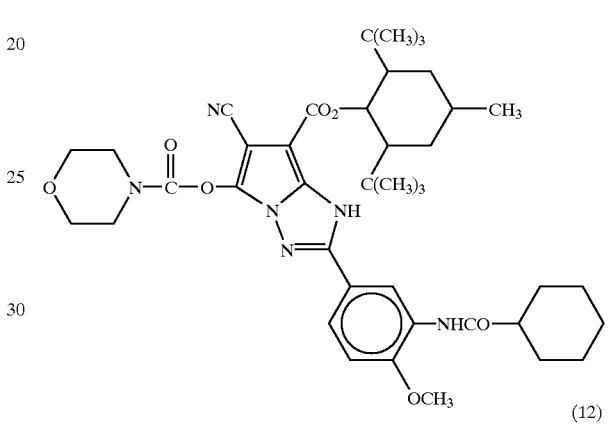
(12)
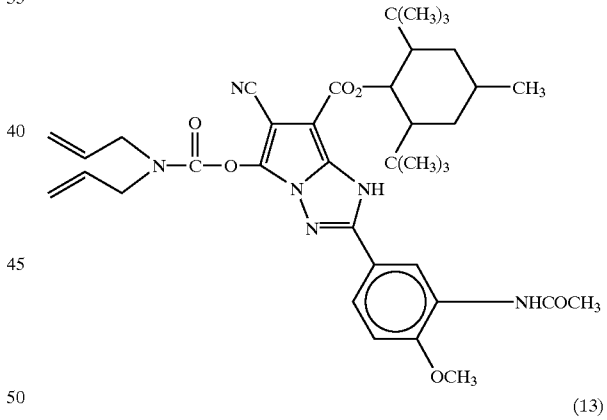
(13)
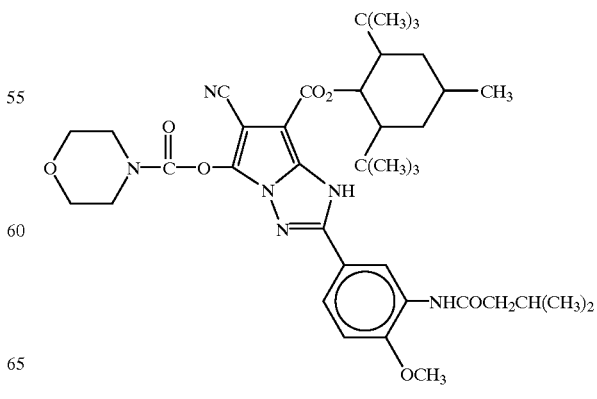

-continued
(14)
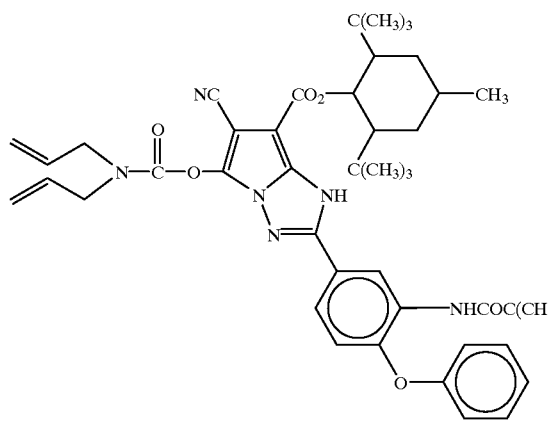
(15)
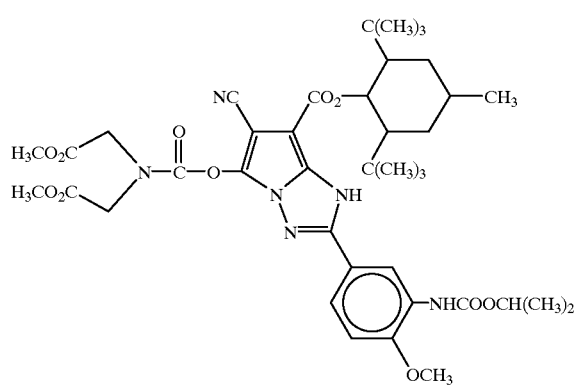
(16)
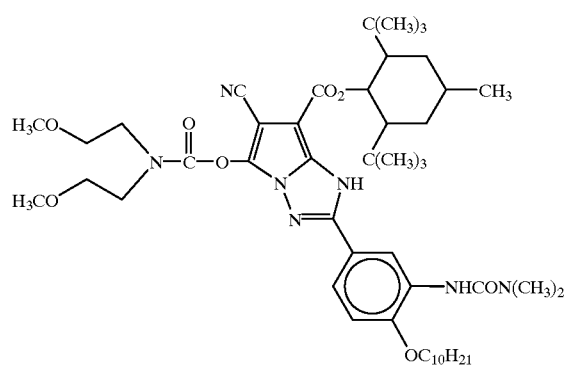
(17)
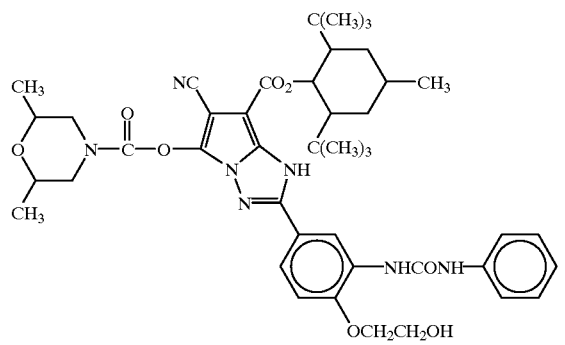
-continued
(18)
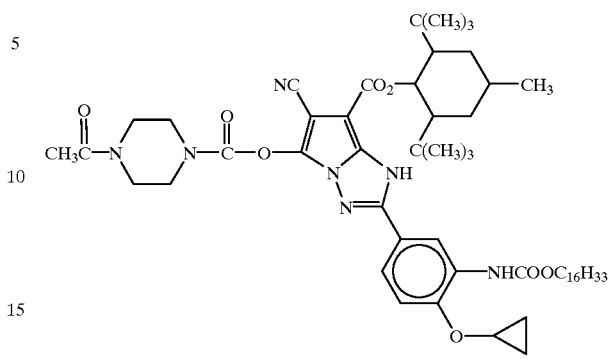
(19)
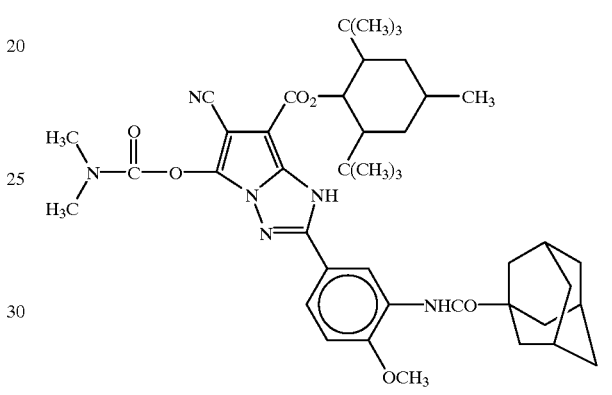
(20)
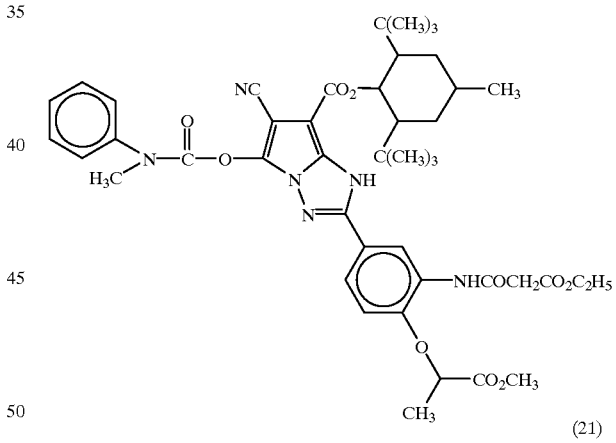
(21)
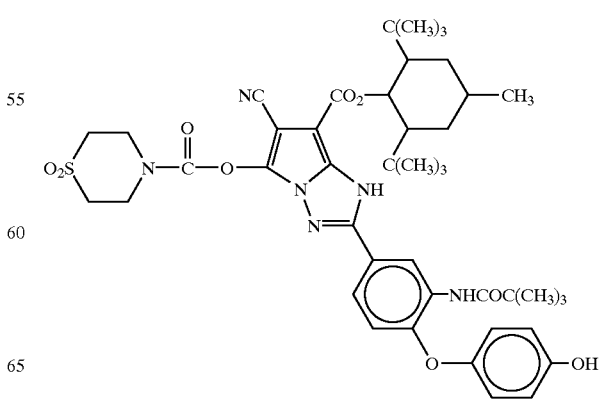

(22)
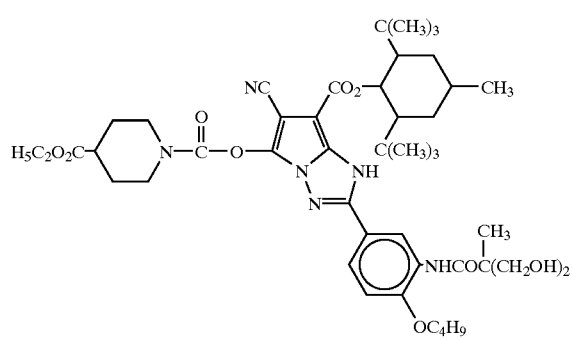
(23)
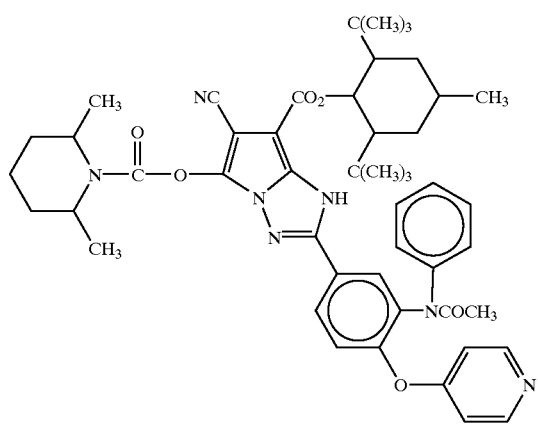
(24)
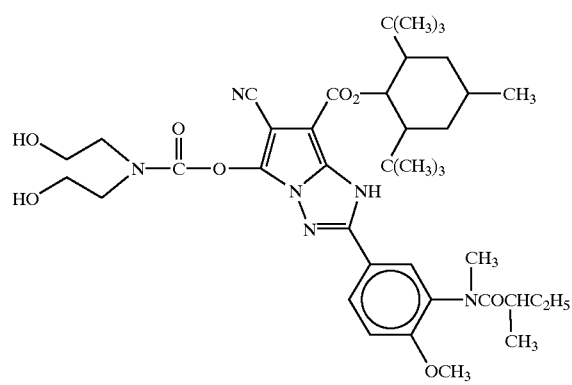
(25)
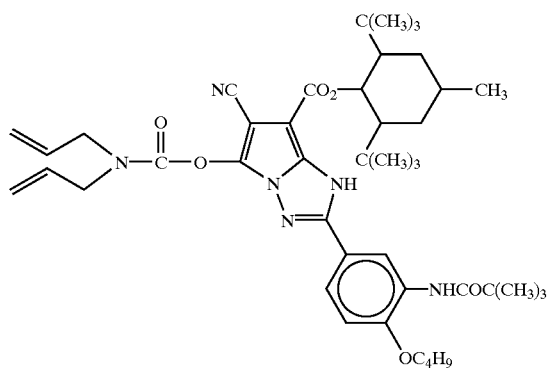
(26)
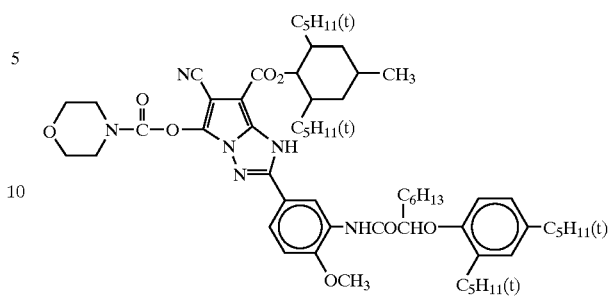
(27)
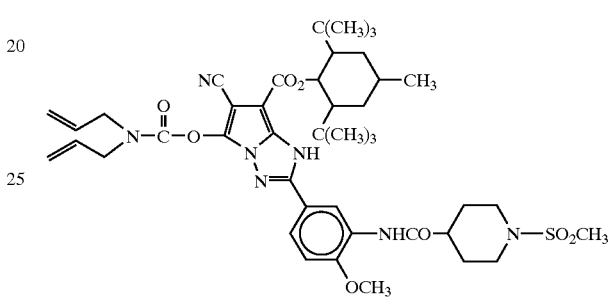
(28)
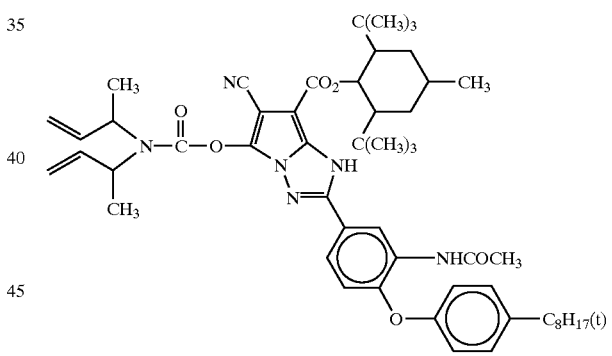
(29)
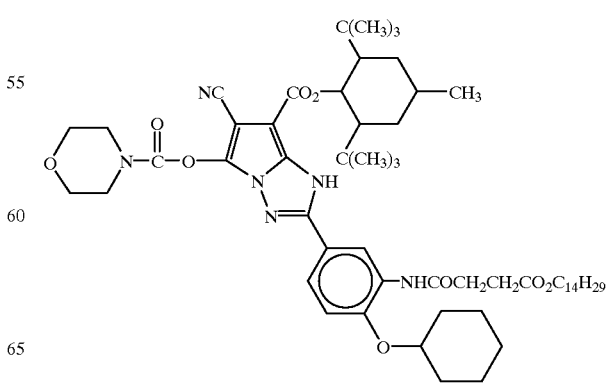

(30) 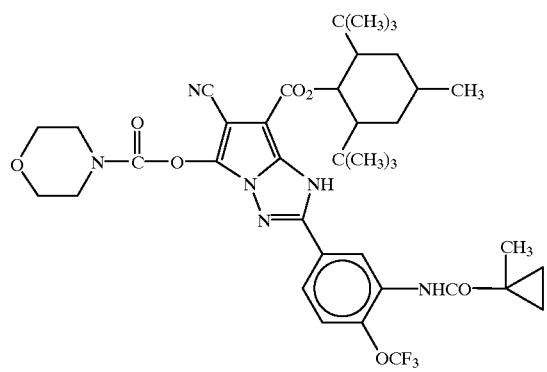
(31) 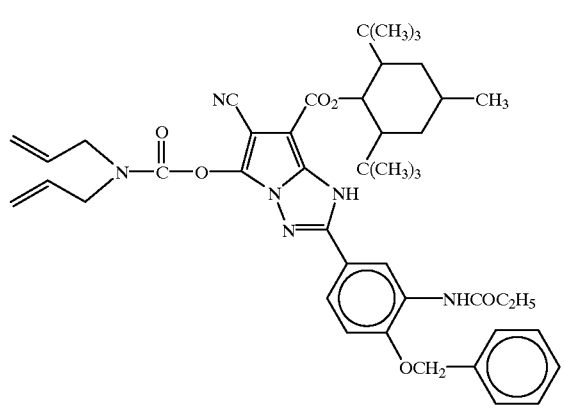
(32) 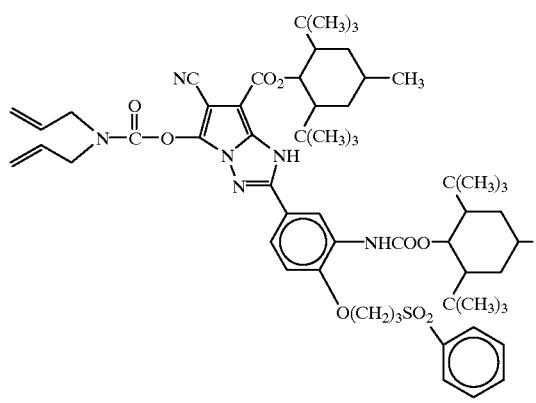
(33) 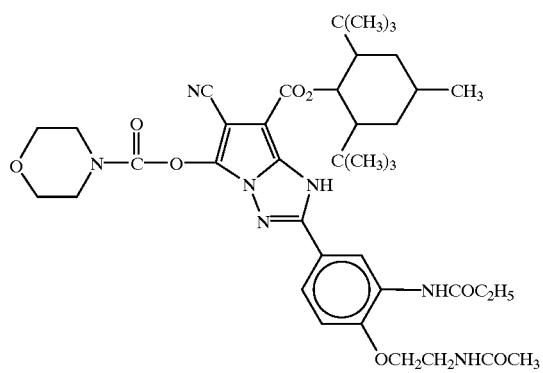
(34) 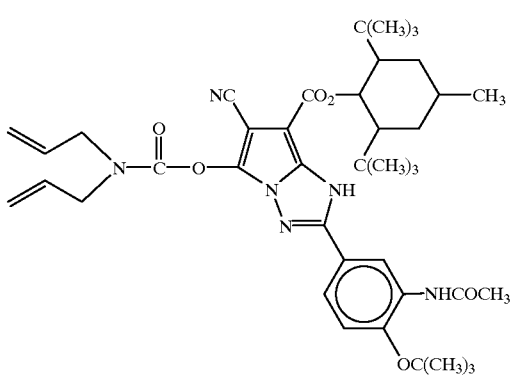
(35) 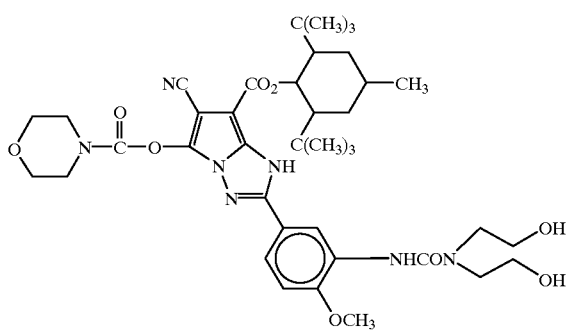
(36) 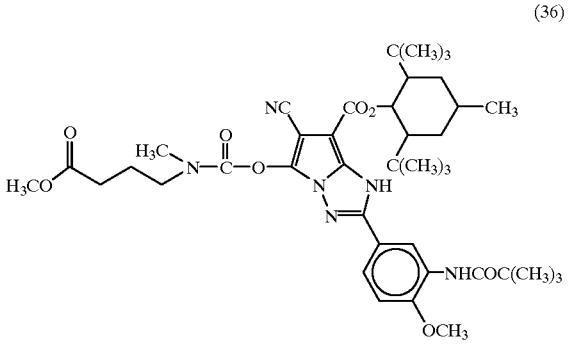
(37) 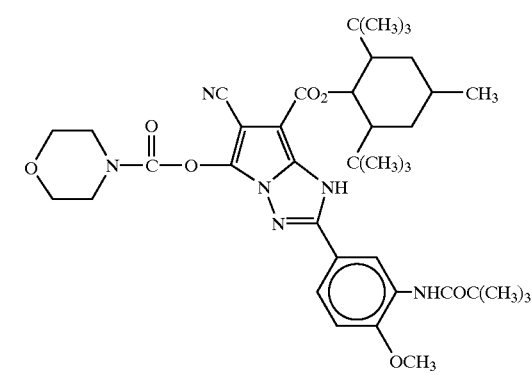

(38)

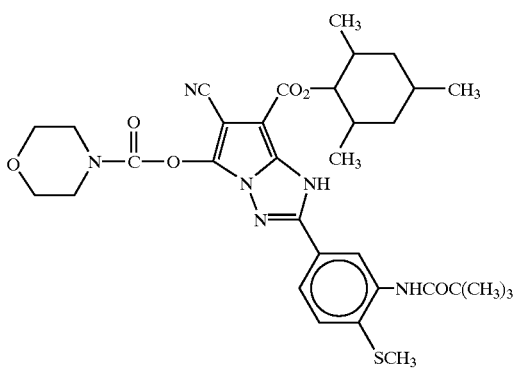

(39)

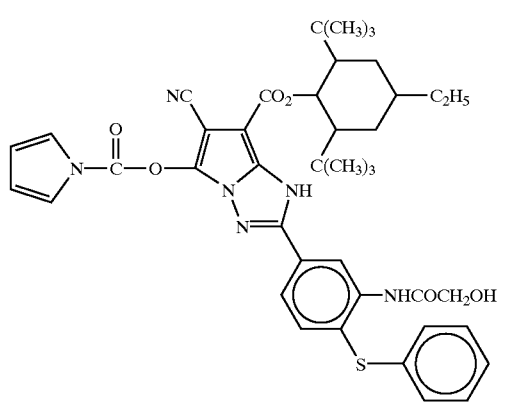

(40)

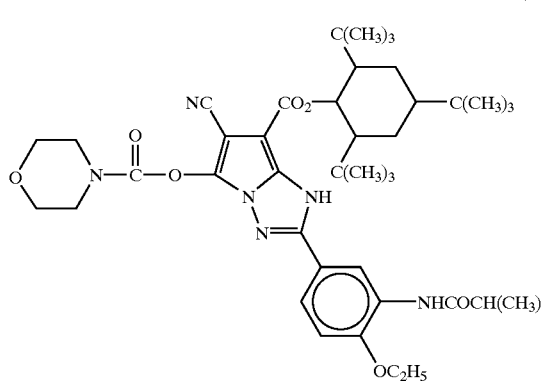

The compound represented by formula (I) of the present invention can be synthesized with reference to the methods described, for example, in JP-A-7-48376 and JP-A-8-109172.

The compound represented by formula (I) of the present invention are useful as a dye-forming compound. The term "dye-forming compound" herein used refers to a compound which is used for dye formation. Further, the term "dye" refers to a compound which has absorption in the range of infrared to visible region. The compound represented by formula (I) of the present invention is more preferably a compound capable of forming a dye which is used for image formation, or which is used as an image-constituting dye. Namely, said compound of the present invention is a dye-forming compound for image formation.

The dye can be easily obtained by reacting the compound of the present invention, represented by formula (I), with, for example, an oxidation product of an aromatic primary amine compound, especially a paraphenylenediamine derivative, an oxidation product of a hydrazine derivative, or a diazonium salt or a releaser thereof. The foregoing method is more specifically described, for example, by Heinrich Zollinger, in Color Chemistry Syntheses, Properties and Applications of Organic Dyes and Pigments (Second, revised edition), VCH Verlagsgesellschaft mbH, Weinheim (Germany), 1991, or a literature referred thereto.

The dyes such as azomethine dyes and azo dyes, preformed by the compound represented by formula (I), may be used as a coloring matter or a dye for image formation. For example, they are used as an ink dye for a printer of the ink jet system, and a dye for dye diffusion transfer system (DTR).

Further, in the system which has a mechanism capable of forming a dye by the use of said compound incorporated therein, dyes may be formed. As to a typical example in this case, use can be made of a coupler for a silver halide color photographic light-sensitive material.

However, the present invention is not limited to the above exemplified use.

In the present invention, the compounds represented by formula (I) are preferably used as a coupler, more preferably as a cyan coupler, and most preferably used in a silver halide color light-sensitive material, especially in a silver halide color photographic light-sensitive material.

Use of the compound of the present invention in the silver halide color photographic light-sensitive material, which is the most preferable embodiment, is explained below.

The light-sensitive material of the present invention essentially has a support and thereon at least one layer containing the coupler of the present invention, in which the layer is essentially a hydrophilic colloid layer. An ordinary light-sensitive material is composed of at least one blue-sensitive silver halide emulsion layer, at least one green-sensitive silver halide emulsion layer, and at least one red-sensitive silver halide emulsion layer, which are coated on a support in this order. The layer configuration may be different from this order. Further, an infrared-sensitive silver halide emulsion layer can be used in place of at least one of the above-mentioned light-sensitive silver halide emulsion layers. A color reproduction owing to the subtractive color process can be performed by these light-sensitive emulsion layers incorporating therein silver halide emulsions each having sensitivity in each corresponding wavelengh region, and a color coupler cable of forming a dye each of which has a relationship of the complementary color with a light to which each of the silver halide emulsion layers is sensitive. However, the light-sensitive emulsion layer and the hue of color obtained by a color coupler may not be designed so as to have such a relationship. It is especially preferred to use the compound of the present invention as a cyan coupler in a red-sensitive silver halide emulsion layer. The content of the coupler of the present invention in a light-sensitive material is generally in the range of $1 \times 10^{-3}$ mole to 1 mole, preferably in the range of $2 \times 10^{-3}$ mole to $5 \times 10^{-1}$ mole, per mole of silver halide in the same layer.

The coupler of the present invention may be incorporated in a light-sensitive material by various known dispersion processes. It is preferred to use an oil-in-water dispersion process in which first a compound is dissolved in a high boiling point organic solvent (in combination with a low boiling point organic solvent as occasion demands), thereby forming a solution and then the resulting solution is emulsified and dispersed in an aqueous gelatin solution, which is then added to a silver halide emulsion. Examples of the high boiling point organic solvent for use the oil-in-water dispersion process are described in, for example, JP-A-5-313327, JP-A-5-323539, JP-A-5-323541, JP-A-6-258803, JP-A-8-262662, and U.S. Pat. No. 2,322,027. Further, the steps, effects and specific examples of latex polymers for impregnation, which are used in the latex dispersion process as one of polymer dispersion process, are described in, for example, U.S. Pat. No. 4,199,363, West German Patent Application (OLS) Nos. 2,541,274 and 2,541,230, JP-B-53-41091 ("JP-B" means examined Japanese patent publication), and European Patent No. 029104. Further, dispersion processes using an organic solvent-soluble polymer are described in, for example, PCT International Publication WO 88/00723 and JP-A-5-150420. Methacrylate-series or acrylamide-series polymers are preferred. In particular, the use of acrylamide-series polymers is preferred, in view of enhancing image stability.

The term "high boiling point" herein used refers to a boiling point of 175° C. or more at ordinary pressure.

Examples of the high boiling point solvent for use in the present invention are described in, for example, U.S. Pat. No. 2,322,027. Specific examples of the high boiling point organic solvent having a boiling point of 175° C. or more at ordinary pressure include phthalic acid esters {e.g., dibutyl phthalate, dicyclohexyl phthalate, di-2-ethylhexyl phthalate, decyl phthalate, bis(2,4-di-tert-amylphenyl) phthalate, bis(2,4-di-tert-amylphenyl) iso-phthalate, bis(1,1-di-ethylpropyl) phthalate}, esters of phosphoric acid or phosphonic acid (e.g., triphenyl phosphate, tricresyl phosphate, 2-ethylhexyldiphenyl phosphate, tricyclohexyl phosphate, tri-2-ethlhexyl phosphate, tridodecyl phosphate, tributoxy-ethyl phosphate, trichloropropyl phosphate, di-2-ethylhexylphenyl phosphonate), benzoic acid esters (e.g., 2-ethylhexyl benzoate, dodecyl benzoate, 2-ethylhexyl p-hydroxybenzoate), amides (e.g., N,N-diethyldodecaneamide, N,N-diethyllaurylamide, N-tetradecylpyrrolidone), sulfonamides (e.g., N-butylbenzenesulfonamide), alcohols and phenols (e.g., isostearyl alcohol, 2,4-di-tert-amylphenol), aliphatic carboxylic acid esters (e.g., bis-(2-ethylhexyl) sebacate, dioctyl azelate, glycerol tributylate, isostearyl lactate, trioctyl citrate), aniline derivatives (e.g., N,N-dibutyl-2-butory-5-tert-octylaniline), hydrocarbones (e.g., paraffin, dodecylbenzene, diisopropylnaphthalate), and chlorinated paraffins. In particular, the foregoing phosphoric acid esters, and hydrogen-donating compounds described in JP-A-6-258803 and JP-A-8-262662 are preferably used, since they help to provide an excellent hue.

In order to reduce a load to environment, it is preferred to use compounds described in European Patent Nos. EP-969320A1 and EP-969321A1, in place of the foregoing phthalic acid esters. In addition to the above-mentioned compounds, tributyl citrate, pentaglycelol triesters and the like may be used.

The dielectric constant of the high boiling point organic solvent varies depending on the purpose for use, but it is preferably in the range of 2.0 to 7.0, more preferably in the range of 3.0 to 6.0.

Further, as an auxiliary solvent, an organic solvent having a boiling point of 30° C. or more, preferably in the range of 50° C. to about 160° C. may be used. Typical examples of the auxiliary solvent include ethyl acetate, butyl acetate, ethyl propionate, methyl ethyl ketone, cyclohexane, 2-ethoxyethyl acetate and dimethylformamide.

All or a part of the auxiliary solvent may be removed from an emulsified dispersion by means of a vacuum distillation, a noodle washing, an ultrafiltration, or the like, as occasion demands for the purpose of improving storage stability with the lapse of time in the state of the emulsified dispersion, or inhibiting a change in photographic properties or enhancing storage stability of photographic properties of the final coating composition in which the emulsified dispersion is mixed with a silver halide emulsion.

The average particle size of the oleophilic fine particle dispersion thus obtained is preferably in the range of 0.001 to 1.0 $\mu$m, more preferably in the range of 0.05 to 0.30 $\mu$m, and most preferably in the range of 0.08 to 0.20 $\mu$m. The average particle size can be determined with a measuring device such as Coulter submicron particle analyser model N4 (Trade name, made by Coulter Electronics Co., Ltd.). If the average particle size of the oleophilic fine particles dispersion is too large, such problems easily arise that a color-formation efficiency of a coupler is lessened, or gloss on the surface of a light-sensitive material deteriorates. In contrast, if the average particle size is too small, viscosity of the dispersion increases and consequently a handling becomes difficult at the time of production.

The amount to be used (in terms of weight ratio) of a dispersion of oleophilic fine particles composed of a coupler of the present invention to a dispersion medium is preferably in the range of 2 to 0.1, more preferably in the range of 1.0 to 0.2, per 1 part of the dispersion medium. Examples of the dispersion medium include hydrophilic polymers, such as gelatin which is a typical example, and in addition thereto mention can be made of polyvinyl alcohol. The oleophilic fine-particle dispersion may contain various compounds, together with the coupler of the present invention, according to the purpose of use.

Known additives may be used with the coupler represented by formula (I) according to the present invention, for the purpose of improving both image fastness and processing-stability, and adjusting a hue.

For example, in order to improve light-resistance (fastness), compounds described in JP-A-5-150426, JP-A-5-150424 and JP-A-5-150423 may be used. In particular, when a compound described in JP-A-5-150424 and a compound described in JP-A-5-150423 are used in combination, they exhibit an outstanding improvement effect. Further, for the purpose of improving both the light resistance at a low-coloring density part and the light stain at a white ground in particular, use of the cyan coupler described in JP-A-5-204110 in addition to the coupler of the present invention, or use of a compound described in U.S. Pat. No. 4,797,350, exhibits an outstanding improvement effect.

Further, it is preferred to use the compound of the present invention, in combination with cyan couplers represented by formula (ADF) described in JP-A-10-333297, as well as in combination with vinyl compounds represented by formula (II), aniline derivatives that have an oxygen-nitrogen bond or that are substituted with an alkoxy group, represented by formula (III), nondiffusion phenidone derivatives represented by formula (IV), nondiffusion carboxylic acids represented by formula (V), nondiffusion arylcarbamoyl derivatives represented by formula (VI), arylamide derivatives represented by formula (VII), and cyclicimide derivatives represented by formula (VII)), each of which are described in JP-A-11-258748. Explanation about each of the foregoing formulae, exemplified specific compounds thereof, and descriptions of synthetic methods and application methods, each of which are described in the above two patent publications, are entirely applied to the present invention. Therefore, these descriptions are incorporated herein into the present specification as a part thereof by reference.

In addition, polymers described in JP-A-8-62797, JP-A-9-171240 and JP-A-9-329861 are preferably used in a hydrophilic colloid layer, in view of inhibiting blix discoloration (leuco dye reciprocity failure) due to a bleaching solution or a bleach-fixing solution.

Compounds for improving dye image stability, such as those described in European Patent No.0277589 A2, are preferably used together with the couplers in the light-sensitive material of the present invention. In particular, it is preferable for such compounds to be used in combination with the pyrrolotriazole coupler represented by formula (I), according to the present invention and/or a pyrazoloazole coupler.

That is, two kinds of compounds described in the foregoing patent specifications, i.e., compounds of the kind which can produce chemically inert, substantially colorless compounds, by combining chemically with an aromatic amine developing agent remaining after color development processing and/or compounds of the kind which can produce chemically inert, substantially colorless compounds, by combining chemically with an oxidized aromatic amine color-developing agent remaining after color development processing, are preferably used in combination or singly. By the use of these compounds, generation of stain which is due to formation of dyes through the reaction between couplers and unoxidized or oxidized color-developing agent remaining in the processed photographic film, and occurrence of other side effects, upon storage after photographic processing, can be inhibited effectively.

Other known photographic materials and additives may be used in the silver halide photographic light-sensitive material of the present invention.

For example, as a photographic support (base), a transmissive type support and a reflective type support may be used. As the transmissive type support, it is preferred to use transparent supports, such as a cellulose nitrate film, and a transparent film of polyethyleneterephthalate, or a polyester of 2,6-naphthalenedicarboxylic acid (NDCA) and ethylene glycol (EG), or a polyester of NDCA, terephthalic acid and EG, provided thereon with an information-recording layer such as a magnetic layer. As the reflective type support, it is especially preferable to use a reflective support having a substrate laminated thereon with a plurality of polyethylene layers or polyester layers (water-proof resin layers or laminate layers), at least one of which contains a white pigment such as titanium oxide.

A more preferable reflective support for use in the present invention is a support having a paper substrate provided with a polyolefin layer having fine holes, on the same side as silver halide emulsion layers. The polyolefin layer may be composed of multi-layers. In this case, it is more preferable for the support to be composed of a fine hole-free polyolefin (e.g., polypropylene, polyethylene) layer adjacent to a gelatin layer on the same side as the silver halide emulsion layers, and a fine hole-containing polyolefin (e.g., polypropylene, polyethylene) layer closer to the paper substrate. The density of the multi-layer or single-layer of polyolefin layer(s) existing between the paper substrate and photographic constituting layers is preferably in the range of 0.40 to 1.0 g/ml, more preferably in the range of 0.50 to 0.70 g/ml. Further, the thickness of the multi-layer or single-layer of polyolefin layer(s) existing between the paper substrate and photographic constituting layers is preferably in the range of 10 to 100 $\mu$m, more preferably in the range of 15 to 70 $\mu$m. Further, the ratio of thickness of the polyolefin layer(s) to the paper substrate is preferably in the range of 0.05 to 0.2, more preferably in the range 0.1 to 0.5.

Further, it is also preferable for enhancing rigidity (mechanical strength) of the reflective support, by providing a polyolefin layer on the surface of the foregoing paper substrate opposite to the side of the photographic constituting layers, i.e., on the back surface of the paper substrate. In this case, it is preferable that the polyolefin layer on the back surface be polyethylene or polypropylene, the surface of which is matted, with the polypropylene being more preferable. The thickness of the polyolefin layer on the back surface is preferably in the range of 5 to 50 $\mu$m, more preferably in the range of 10 to 30 $\mu$m, and further the density thereof is preferably in the range of 0.7 to 1.1 g/ml. As to the reflective support for use in the present invention, preferable embodiments of the polyolefin layer provide on the paper substrate include those described in JP-A-10-333277, JP-A-10-333278, JP-A-11-52513, JP-A-11-65024, European Patent Nos. 0880065 and 0880066.

Further, it is preferred that the above-described water-proof resin layer contains a fluorescent whitening agent. Further, the fluorescent whitening agent also may be dispersed in a hydrophilic colloid layer of the light-sensitive material. Preferred fluorescent whitening agents which can be used, include benzoxazole series, coumarin series, and pyrazoline series compounds. Further, fluorescent whitening agents of benzoxazolylnaphthalene series and benzoxazolyl-stilbene series are more preferably used. The amount of the fluorescent whitening agent to be used is not particularly limited, and preferably in the range of 1 to 100 mg/m$^2$. When a fluorescent whitening agent is mixed with a water-proof resin, a mixing ratio of the fluorescent whitening agent to be used in the water-proof resin is preferably in the range of 0.0005 to 3% by weight, and more preferably in the range of 0.001 to 0.5% by weight of the resin.

Further, a transmissive type support or the foregoing reflective type support each having coated thereon a hydrophilic colloid layer containing a white pigment may be used as the reflective type support.

Furthermore, a reflective type support having a mirror plate reflective metal surface or a secondary diffusion reflective metal surface may be employed as the reflective type support.

As the support for use in the light-sensitive material of the present invention, a support of the white polyester type, or a support provided with a white pigment-containing layer on the same side as the silver halide emulsion layer, may be adopted for display use. Further, it is preferable for improving sharpness that an antihalation layer be provided on the silver halide emulsion layer side or the reverse side of the support. In particular, it is preferable that the transmission density of support be adjusted to the range of 0.35 to 0.8 so that a display may be enjoyed by means of both transmitted and reflected rays of light.

In the light-sensitive material of the present invention, in order to improve, e.g., the sharpness of an image, a dye (particularly an oxonole-series dye) that can be discolored by processing, as described in European Patent No. 0337490 A2, pages 27 to 76, is preferably added to the hydrophilic colloid layer such that an optical reflection density at 680 nm in the light-sensitive material is 0.70 or more. It is also preferable to add 12% by weight or more (more preferably 14% by weight or more) of titanium oxide that is surface-treated with, for example, dihydric to tetrahydric alcoholes (e.g., trimethylolethane) to a water-proof resin layer of the support.

The light-sensitive material of the present invention preferably contains, in their hydrophilic colloid layers, dyes (particularly oxonole dyes and cyanine dyes) that can be discolored by processing, as described in European Patent No. 0337490 A2, pages 27 to 76, in order to prevent irradiation or halation or enhance safelight safety (immunity). Further, dyes described in European Patent No. 0819977 are also preferably used in the present invention.

Among these water-soluble dyes, some deteriorate color separation or safelight safety when used in an increased amount. Preferable examples of the dye which can be used and which does not deteriorate color separation include water-soluble dyes described in JP-A-5-127324, JP-A-5-127325 and JP-A-5-216185.

In the present invention, it is possible to use a colored layer which can be discolored during processing, in place of the water-soluble dye, or in combination with the water-soluble dye. The colored layer capable of being discolored with a processing to be used may contact with an emulsion layer directly, or indirectly through an interlayer containing an agent for preventing a color-mixing during processing, such as gelatin and hydroquinone. The colored layer is preferably provided as a lower layer (closer to a support) with respect to the emulsion layer which develops the same primary color as the color of the colored layer. It is possible to provide colored layers independently, each corresponding to respective primary colors. Alternatively, only one layer selected from them may be provided. In addition, it is possible to provide a colored layer subjected to coloring so as to match a plurality of primary-color regions. About the optical reflection density of the colored layer, it is preferred that at the wavelength which provides the highest optical density in a range of wavelengths used for exposure (a visible light region from 400 nm to 700 nm for an ordinary printer exposure, and the wavelength of the light generated from the light source in the case of scanning exposure), the optical density is within the range of 0.2 to 3.0, more preferably 0.5 to 2.5, and particularly preferably 0.8 to 2.0.

The colored layer described above may be formed by a known method. For example, there are a method in which a dye in a state of a dispersion of solid fine particles is incorporated in a hydrophilic colloid layer, as described in JP-A-2-282244, from page 3, upper right column to page 8, and JP-A-3-7931, from page 3, upper right column to page 11, left under column; a method in which an anionic dye is mordanted in a cationic polymer, a method in which a dye is adsorbed onto fine grains of silver halide or the like and fixed in the layer, and a method in which a colloidal silver is used as described in JP-A-1-239544. As to a method of dispersing fine-powder of a dye in solid state, for example, JP-A-2-308244, pages 4 to 13 describes a method in which solid fine particles of dye which is at least substantially water-insoluble at the pH of 6 or less, but at least substantially water-soluble at the pH of 8 or more, are incorporated. The method of mordanting anionic dyes in a cationic polymer is described, for example, in JP-A-2-84637, pages 18 to 26. U.S. Pat. Nos. 2,688,601 and 3,459,563 disclose a method of preparing a colloidal silver for use as a light absorber. Among these methods, preferred are the methods of incorporating fine particles of dye and of using a colloidal silver.

Silver halide grains in the silver halide emulsion which can be used in the present invention, are preferably cubic or tetradecahedral crystal grains substantially having {100} planes (these grains may be rounded at the apexes thereof and further may have planes of higher order), or octahedral crystal grains. Further, a silver halide emulsion in which the proportion of tabular grains having an aspect ratio of 2 or more and composed of {100} or {111} planes accounts for 50% or more in terms of the total projected area, can also be preferably used. The term "aspect ratio" refers to the value obtained by dividing the diameter of the circle having an area equivalent to the projected area of an individual grain by the thickness of the grain. In the present invention, cubic grains, or tabular grains having {100} planes as major faces, or tabular grains having {111} planes as major faces are preferably used.

As a silver halide emulsion which can be used in the present invention, for example, silver chloride, silver bromide, silver iodobromide, or silver chloro(iodo)bromide emulsions may be used. It is preferable for a rapid processing to use a silver chloride, or silver chlorobromide emulsions having a silver chloride content of 95 mole % or greater, more preferably a silver halide emulsion having a silver chloride content of 98 mole % or greater. Especially preferred of these silver halide emulsions are those containing silver chloride grains having a silver bromide localized phase on the surface thereof, since both a high sensitivity and a stabilization of photographic properties are attained by the silver bromide localized phase. Further, it is also preferred to use silver halide grains having in their shell parts a silver iodochloride phase of 0.01 to 0.50 mole %, more preferably 0.10 to 0.40 mole %, per mole of the total silver, in view of a high sensitivity and an excellent high illumination intensity exposure suitability.

The silver bromide localized phase is preferably formed by epitaxial growth of the localized phase having a total silver bromide content of at least 10 mole % in the silver bromide localized phase. A silver bromide content of the silver bromide localized phase is preferably in the range of 10 to 60 mole %, and most preferably in the range of 20 to 50 mole %. The silver bromide localized phase is preferably composed of silver having population of 0.1 to 5 mole %, more preferably 0.3 to 4 mole % to the molar amount of entire silver which constitutes silver halide grains for use in the present invention. The silver bromide localized phase is preferably doped with complex ions of metals of Group VIII, such as iridium (III) chloride, iridium (III) bromide, iridium(IV) chloride, sodium hexachloroiridate (III), potassium hexachloroiridate (IV), hexaammineiridium(IV) salts, trioxalatoiridium(III) salt, and trioxalatoiridium(IV) salt. The amount of these compounds to be added can be varied in a wide range depending on the purposes, and is preferably in the range of $10^{-9}$ to $10^{-2}$ mole per mole of silver halide.

In a silver halide emulsion for use in the present invention, various kinds of polyvalent metal ion impurities other than iridium may be incorporated, during grain formation or in the course of physical ripening of the emulsion. As for examples of the impurities to be used, salts or complex salts of metals of Group VIII of the Periodic table, such as iron, ruthenium, osmium, rhenium, rhodium, cadmium, zinc, lead, copper and thallium may be used in combination thereof. In the present invention, compounds of metals such as iron, ruthenium, osmium and rhenium, which have at least 4 cyano ligands, are particularly preferred, since a high illumination intensity sensitivity is further enhanced and latent image sensitization is also inhibited. Iridium compounds provide an outstanding effect on the high-illumination intensity exposure suitability. The amount of these compounds to be added can be varied in a wide range depending on the purposes, and is preferably in the range of $10^{-9}$ mole to $10^{-2}$ mole, per mole of silver halide.

The silver halide grains in the silver halide emulsion for use in the present invention have an average grain size (the grain size herein refers to the diameter of the circle equivalent to the projected area of the grain, and the number average is taken as the average grain size) of preferably from 0.1 μm to 2 μm.

With respect to the distribution of sizes of these grains, so called monodisperse emulsion having a variation coefficient (the value obtained by dividing the standard deviation of the grain size distribution by the average grain size) of 20% or less, more preferably 15% or less, and further preferably 10% or less, is preferred. For obtaining a wide latitude, it is also preferred to blend the above-described monodisperse emulsions in the same layer or to form a multilayer structure using the monodisperse emulsions.

Various compounds or precursors thereof can be included in the silver halide emulsion for use in the present invention to prevent fogging from occurring or to stabilize photographic performance during manufacture, storage or photographic processing of the photographic material. Specific examples of compounds useful for the above purposes are disclosed in JP-A-62-215272, pages 39 to 72, and they can be preferably used. In addition, 5-arylamino-1,2,3,4-thiatriazole compounds (the aryl residual group has at least one electron-attractive group) disclosed in European Patent No. 0447647 are also preferably used.

Further, in the present invention, it is preferable for enhancing stability of the silver halide emulsion to use hydroxamic acid derivatives described in JP-A-11-109576, cyclic ketones having a double bond both ends of which are substituted with an amino group or a hydroxyl group, in adjacent to a carbonyl group, described in JP-A-11-327094 (particularly those represented by formula (SI) and the descriptions of paragraph numbers 0036 to 0071 of JP-A-11-327094 can be incorporated in the specification of this application by reference), catechols and hydroquinones each substituted with a sulfo group, described in JP-A-11-143011 (e.g., 4,5-dihydroxy-1,3-benzenedisulfonic acid, 2,5-dihydroxy-1,4-benzenedisulfonic acid, 3,4-dihydroxybenzenesulfonic acid, 2,3-dihydroxybenzenesulfonic acid, 2,5-dihydroxybenzenesulfonic acid, 3,4,5-trihydroxybenzenesulfonic acid, and salts thereof), and water-soluble reducing agents represented by formula (I) to (III) of JP-A-11-102045.

Spectral sensitization is carried out for the purpose of imparting spectral sensitivity in a desired light wavelength region to the light-sensitive emulsion in each layer of the photographic material of the present invention.

Spectral sensitizing dyes which are used in the photographic material of the present invention for spectral sensitization of blue, green and red light region include those disclosed by F. M. Harmer, in *Heterocyclic Compounds— Cyanine Dyes and Related Compounds*, John Wiley & Sons, New York, London (1964). Specific examples of compounds and spectral sensitization processes that are preferably used in the present invention include those described in JP-A-62-215272, from page 22, right upper column to page 38. In addition, the spectral sensitizing dyes described in JP-A-3-123340 are very preferred as red-sensitive spectral sensitizing dyes for silver halide emulsion grains having a high silver chloride content from the viewpoint of stability, adsorption strength and the temperature dependency of exposure, and the like.

The amount of these spectral sensitizing dyes to be added can be varied in a wide range depending on the occasion, and is preferably in the range of $5 \times 10^{-6}$ mole to $1.0 \times 10^{-2}$ mole, more preferably in the range of $1.0 \times 10^{-6}$ mole to $5.0 \times 10^{-3}$ mole, per mole of silver halide.

The silver halide emulsion that can be used in the present invention are generally chemically sensitized. Chemical sensitization can be performed by utilizing a sulfur sensitization, represented by the addition of an unstable sulfur compound, noble metal sensitization represented by gold sensitization, and reduction sensitization, each singly or in combination thereof. Compounds that are preferably used for chemical sensitization include those described in JP-A-62-215272, from page 18, right lower column to page 22, right upper column. Of these chemical sensitization, gold-sensitized silver halide emulsion are particularly preferred, since a change in photographic properties which occurs when scanning exposure to laser beams or the like is conducted, can be further reduced by gold sensitization. In order to conduct gold sensitization, compounds such as chloroauric acid or a salt thereof, gold thiocyanates, gold thiosulfates, and colloidal gold sulfide may be used. The amount of these compounds to be added can be varied in a wide range depending on the occasion, and is generally in the range of $5 \times 10^{-7}$ mole to $5 \times 10^{-3}$ mole, preferably in the range of $1.0 \times 10^{-6}$ mole to $1 \times 10^{-4}$ mole, per mole of silver halide. In the present invention, gold sensitization may be used in combination with other sensitizing methods, for example, sulfur sensitization, selenium sensitization, tellurium sensitization, reduction sensitization, or noble metal sensitization using a noble metal compound other than gold compounds.

The silver halide photographic light-sensitive material of the present invention can be used for a color negative film, a color positive film, a color reversal film, a color reversal photographic printing paper, a color photographic printing paper and the like. Among these materials, the light-sensitive material of the present invention is preferably used for a color photographic printing paper.

The color photographic printing paper preferably has at least one yellow color-forming silver halide emulsion layer, at least one magenta color-forming silver halide emulsion layer, and at least one cyan color-forming silver halide emulsion layer, on a support. Generally, these silver halide emulsion layers are in the order, from the support, of the yellow color-forming silver halide emulsion layer, the magenta color-forming silver halide emulsion layer and the cyan color-forming silver halide emulsion layer.

However, another layer arrangement which is different from the above, may be adopted.

In the present invention, a yellow coupler-containing silver halide emulsion layer may be disposed at any position on a support. However, in the case where silver halide tabular grains are contained in the yellow coupler-containing layer, it is preferable that the yellow coupler-containing layer be positioned more appart from a support than at least one of a magenta coupler-containing silver halide emulsion layer and a cyan coupler-containing silver halide emulsion layer. Further, it is preferable that the yellow coupler-containing silver halide emulsion layer be positioned most appart from a support of other silver halide emulsion layers, from the viewpoint of color-development acceleration, desilvering acceleration, and reduction in a residual color due to a sensitizing dye. Further, it is preferable that the cyan coupler-containing silver halide emulsion layer be disposed in the middle of other silver halide emulsion layers, from the viewpoint of reduction in a blix fading. On the other hand, it is preferable that the cyan coupler-containing silver halide emulsion layer be the lowest layer, from the viewpoint of reduction in a light fading. Further, each of a yellow-color-forming layer, a magenta-color-forming layer and a cyan-color-forming layer may be composed of two or three layers. It is also preferable that a color forming layer be formed by disposing a silver halide emulsion-free layer containing a coupler in adjacent to a silver halide emulsion layer, as described in, for example, JP-A-4-75055, JP-A-9-114035, JP-A-10-246940, and U.S. Pat. No. 5,576,159.

Preferred examples of silver halide emulsions and other materials (additives or the like) for use in the present invention, photographic constitutional layers (arrangement of the layers or the like), and processing methods for processing the photographic materials and additives for processing are disclosed in JP-A-62-215272, JP-A-2-33144 and European Patent No. 0355660 A2. Particularly, those disclosed in European Patent No. 0355660 A2 are preferably used. Further, it is also preferred to use silver halide color photographic light-sensitive materials and processing methods therefor disclosed in, for example, JP-A-5-34889, JP-A-4-359249, JP-A-4-313753, JP-A-4-270344, JP-A-5-66527, JP-A-4-34548, JP-A-4-145433, JP-A-2-854, JP-A-1-158431, JP-A-2-90145, JP-A-3-194539, JP-A-2-93641 and European Patent Publication No. 0520457 A2.

In particular, as the above-described reflective support and silver halide emulsion, as well as the different kinds of metal ions to be doped in the silver halide grains, the storage stabilizers or antifogging agents of the silver halide emulsion, the methods of chemical sensitization (sensitizers), the methods of spectral sensitization (spectral sensitizing dyes), the cyan, magenta, and yellow couplers and the emulsifying and dispersing methods thereof, the dye stability-improving agents (stain inhibitors and discoloration inhibitors), the dyes (coloring layers), the kinds of gelatin, the layer structure of the light-sensitive material, and the film pH of the light-sensitive material, those described in the patent publications as shown in the following Table 1 are preferably used in the present invention.

TABLE 1

| Element | JP-A-7-104448 | JP-A-7-77775 | JP-A-7-301895 |
|---|---|---|---|
| Reflective-type bases | Column 7, line 12 to Column 12, line 19 | Column 35, line 43 to Column 44, line 1 | Column 5, line 40 to Column 9, line 26 |
| Silver halide emulsions | Column 72, line 29 to Column 74, line 18 | Column 44, line 36 to Column 46, line 29 | Column 77, line 48 to Column 80, line 28 |
| Different metal ion species | Column 74, lines 19 to 44 | Column 46, line 30 to Column 47, line 5 | Column 80, line 29 to Column 81, line 6 |
| Storage stabilizers or antifoggants | Column 75, lines 9 to 18 | Column 47, lines 20 to 29 | Column 18, line 11 to Column 31, line 37 (Especially, mercaptoheterocyclic compounds) |
| Chemical sensitizing methods (Chemical sensitizers) | Column 74, line 45 to Column 75, line 6 | Column 47, lines 7 to 17 | Column 81, lines 9 to 17 |
| Spectrally sensitizing methods (Spectral sensitizers) | Column 75, line 19 to Column 76, line 45 | Column 47, line 30 to Column 49, line 6 | Column 81, line 21 to Column 82, line 48 |
| Cyan couplers | Column 12, line 20 to Column 39, line 49 | Column 62, line 50 to Column 63, line 16 | Column 88, line 49 to Column 89, line 16 |
| Yellow couplers | Column 87, line 40 to Column 88, line 3 | Column 63, lines 17 to 30 | Column 89, lines 17 to 30 |
| Magenta couplers | Column 88, lines 4 to 18 | Column 63, line 3 to Column 64, line 11 | Column 31, line 34 to Column 77, line 44 and column 88, lines 32 to 46 |
| Emulsifying and dispersing methods of couplers | Column 71, line 3 to Column 72, line 11 | Column 61, lines 36 to 49 | Column 87, lines 35 to 48 |
| Dye-image-preservability improving agents (antistaining agents) | Column 39, line 50 to Column 70, line 9 | Column 61, line 50 to Column 62, line 49 | Column 87, line 49 to Column 88, line 48 |
| Anti-fading agents | Column 70, line 10 to Column 71, line 2 | | |
| Dyes (coloring layers) | Column 77, line 42 to Column 78, line 41 | Column 7, line 14 to Column 19, line 42, and Column 50, line 3 to Column 51, line 14 | Column 9, line 27 to Column 18, line 10 |
| Gelatins | Column 78, lines 42 to 48 | Column 51, lines 15 to 20 | Column 83, lines 13 to 19 |
| Layer construction of light-sensitive materials | Column 39, lines 11 to 26 | Column 44, lines 2 to 35 | Column 31, line 38 to Column 32, line 33 |
| pH of coatings of light-sensitive material | Column 72, lines 12 to 28 | | |
| Scanning exposure | Column 76, line 6 to Column 77, line 41 | Column 49, line 7 to Column 50, line 2 | Column 82, line 49 to Column 83, line 12 |
| Preservatives in developing solution | Column 88, line 19 to Column 89, line 22 | | |

As other cyan, magenta and yellow couplers which can be used in combination in the present invention, those disclosed in JP-A-62-215272, page 91, right upper column line 4 to page 121, left upper column line 6, JP-A-2-33144, page 3, right upper column line 14 to page 18, left upper column bottom, and page 30, right upper column line 6 to page 35, right under column, line 11, European Patent No. 0355,660 (A2), page 4 lines 15 to 27, page 5 line 30 to page 28 bottom line, page 45 lines 29 to 31, page 47 line 23 to page 63 line 50, are also advantageously used.

Further, it is preferred for the present invention to add compounds represented by formula (II) or (III) in WO 98/33760 and compounds represented by formula (D) described in JP-A-10-221825.

These are further specifically explained below.

As the cyan coupler which can be used together with the cyan coupler of the present invention, the use in combination with phenol series or naphthol series cyan couplers is preferred as mentioned above. For example, cyan couplers represented by formula (ADF) described in JP-A-10-333297 are preferred.

As cyan couplers other than the foregoing cyan couplers, which are preferably used in combination, there are pyrroloazole cyan couplers described in European Patent Nos. 0488248 and 0491197, 2,5-diacylaminophenol couplers described in U.S. Pat. No. 5,888,716, pyrazoloazole cyan couplers having an electron-withdrawing group or a hydrogen-bond group at the 6-position, described in U.S. Pat. Nos. 4,873,183 and 4,916,051, and particularly pyrazoloazole cyan couplers having a carbamoyl group at the 6-position, described in JP-A-8-171185, JP-A-8-311360 and JP-A-8-339060.

In addition, the cyan coupler of the present invention can also be used together with a diphenylimidazole-series cyan coupler described in JP-A-2-33144; a 3-hydroxypyridine-series cyan coupler (particularly a coupler (42), which is a 2-equivalent coupler formed by allowing a 4-equivalent coupler to have a chlorine splitting-off group, and couplers (6) and (9), enumerated as specific examples are particularly preferable) described in EP 0333185 A2; a cyclic active methylene-series cyan coupler (particularly couplers 3, 8, and 34 enumerated as specific examples are particularly preferable) described in JP-A-64-32260; a pyrrolopyrozole cyan coupler described in European Patent No. 0456226 A1; or a pyrroloimidazole cyan coupler described in European Patent No. 0484909.

As yellow couplers, also preferably used in the present invention are acylacetamide yellow couplers in which the acyl group has a 3-membered to 5-membered cyclic structure, such as those described in European Patent No. 0447969 A1; malondianilide yellow couplers having a cyclic structure, as described in European Patent No. 0482552 A1; acylacetamide yellow couplers having a dioxane structure such as those described in U.S. Pat. No. 5,118,599, in addition to the compounds described in the above-mentioned table. Above all, acylacetamide yellow couplers in which the acyl group is an 1-alkylcyclopropane-1-carbonyl group, and malondianilide yellow couplers in which one anilide constitute an indoline ring are especially preferably used. These couplers may be used singly or as combined.

The magenta couplers usable in the present invention are 5-pyrazolone magenta couplers and pyrazoloazole magenta couplers such as those described in the above-mentioned patent publications in the above Table. Among these, preferred are pyrazolotriazole couplers in which a secondary or tertiary alkyl group is directly bonded to the 2-, 3- or 6-position of the pyrazolotriazole ring, such as those described in JP-A-61-65245; pyrazoloazole couplers having a sulfonamido group in its molecule, such as those described in JP-A-61-65246; pyrazoloazole couplers having an alkoxyphenylsulfonamido ballasting group, such as those described in JP-A-61-147254; and pyrazoloazole couplers having a 6-positioned alkoxy or aryloxy group, such as those described in European Patent Nos. 0226849 A2 and 0294785 A, in view of the hue and stability of image to be formed therefrom and color-forming property of the couplers.

Particularly as the magenta coupler, pyrazoloazole couplers represented by formula (M—I) described in JP-A-8-122984 are preferred. The descriptions of paragraph Nos. 0009 to 0026 of the patent publication are entirely applied to the present invention and therefore are incorporated in the specification of this application as a part thereof by reference.

In addition, pyrazoloazole couplers having a steric hindrance group at both the 3- and 6-positions, as described in European Patent Nos. 845384 and 884640, are also preferably used.

It is preferred that magenta or yellow couplers as well as the cyan couplers of the present invention are also pregnated into loadable latex polymers (as described, for example, in U.S. Pat. No. 4,203,716) in the presence (or absence) of the high boiling point organic solvents described in the foregoing table, or they are dissolved in the presence (or absence) of the foregoing high boiling point organic solvents with a polymer insoluble in water but soluble in an organic solvent, and then emulsified and dispersed into aqueous hydrophilic colloid solution.

The water-insoluble but organic solvent-soluble polymers which can be preferably used, include the homo-polymers and co-polymers disclosed in U.S. Pat. No. 4,857,449, from column 7 to column 15 and WO 88/00723, from page 12 to page 30. The use of methacrylate-series or acrylamide-series polymers, especially acrylamide-series polymers are more preferable in view of color image stabilization and the like.

In the present invention, known color mixing-inhibitors may be used. Among these compounds, those described in the following patent publications are preferred.

For example, high molecular weight redox compounds described in JP-A-5-333501; phenidone- or hydrazine-series compounds as described in, for example, WO 98/33760 and U.S. Pat. No. 4,923,787; and white couplers as described in, for example, JP-A-5-249637, JP-A-10-282615 and German Patent No. 1962914 A1, may be used. Further, in order to accelerate a developing speed by increasing the pH of a developing solution, redox compounds described in, for example, German Patent Nos. 19,618,786 A1 and 19,806, 846 A1, European Patent Nos. 0,839,623 A1 and 0,842,975 A1, and French Patent No. 2,760,460 A1, are also preferably used.

In the present invention, as an ultraviolet ray absorbent, it is preferred to use compounds having a high molar extinction coefficient. Examples of these compounds include those having a triazine skeleton. Among these compounds, use can be made of those described, for example, in JP-A-46-3335, JP-A-55-152776, JP-A-5-197074, JP-A-5-232630, JP-A-5-307232, JP-A-6-211813, JP-A-8-53427, JP-A-8-234364, JP-A-8-239368, JP-A-9-31067, JP-A-10-115898, JP-A-10-147577, JP-A-10-182621, JP-T-8-501291 ("JP-T" means searched and published International patent application), European Patent No. 0,711,804 A1 and German Patent No. 19,739,797A.

As the binder or hydrophilic colloid which can be used in photographic layers to constitute the light-sensitive material of the present invention, gelatin is used advantageously, but another hydrophilic colloid can be used singly or in combination with gelatin. In particular, it is preferable for the gelatin for use in the present invention that the content of heavy metals, such as Fe, Cu, Zn and Mn, as impurities therein, be reduced to 5 ppm or below, more preferably 3 ppm or below.

Further, the amount of calcium contained in the light-sensitive material is preferably 20 mg/m² or less, more preferably 10 mg/m² or less, and most preferably 5 mg/m² or less.

In the present invention, it is preferred to add an antibacterial (fungi-preventing) agent and antimold agent, as described in JP-A-63-271247, in order to destroy various kinds of molds and bacteria which propagate in a hydrophilic colloid layer and deteriorate the image.

Further, the pH of the film of the light-sensitive material is preferably in the range of 4.0 to 7.0, more preferably in the range of 4.0 to 6.5.

In the present invention, a surface-active agent may be added to the light-sensitive material, in view of improvement in coating-stability, prevention from generation of static electricity and adjustment of charge amount. As the surface-active agent, there are anionic, cationic, betaine and nonionic surfactants. Examples thereof include those described in JP-A-5-333492. As the surface-active agent for use in the present invention, a fluorine-containing surface-active agent is preferred. In particular, fluorine-containing surface-active agents as shown below can be preferably used.

The amount of these surface-active agents to be added to the light-sensitive material is not particularly limited, but generally in the range of $1\times10^{-5}$ to 1 g/m², preferably in the range of $1\times10^{-4}$ to $1\times10^{-1}$ g/m², more preferably in the range of $1\times10^{-3}$ to $1\times10^{-2}$ g/m².

These fluorine-containing surface-active agents may be used singly or in combination with known other surface-active agents, but they are preferably used together with such known other surface-active agents.

The light-sensitive material of the present invention can preferably be used, in addition to the printing system using a general negative printer, in a scanning exposure system using a cathode ray tube (CRT).

The cathode ray tube exposure apparatus is simpler and more compact, and therefore less expensive than a laser-emitting apparatus. Further, optical axis and color (hue) can easily be adjusted.

In a cathode ray tube which is used for image-wise exposure, various light-emitting materials which emit a light in the spectral region, are used as occasion demands. For example, any one of red-light-emitting materials, green-light-emitting materials, blue-light-emitting materials, or a mixture of two or more of these light-emitting materials may be used. The spectral regions are not limited to the above red, green and blue, and fluorophoroes which can emit a light in a region of yellow, orange, purple or infrared can be used. Particularly, a cathode ray tube which emits a white light by means of a mixture of these light-emitting materials, is often used.

In the case where the light-sensitive material has a plurality of light-sensitive layers each having different spectral sensitivity distribution from each other and also the cathode ray tube has a fluorescent substance which emits light in a plurality of spectral regions, exposure to a plurality of colors

| Anionic | | |
|---|---|---|
| FS-1 | $[F(CF_2CF_2)_nCH_2CH_2O]_xPO(O^-M^+)_y$ | $M^+ = H^+, NH_4^+$ $x + y = 3, n = 1\sim7$ |
| FS-2 | $[F(CF_2CF_2)_nCH_2CH_2O]_xPO(O^-M^+)_y(OCH_2CH_2OH)_z$ | $M^+ = H^+, NH_4^+$ $x + y + z = 3, n = 1\sim7$ |
| FS-3 | $F(CF_2CF_2)_nCH_2CH_2SO_3^-M^+$ | $M^+ = H^+, NH_4^+$ $n = 1\sim9$ |
| FS-4 | $C_6F_{13}CH_2CH_2SO_3^-M^+$ | $M^+ = H^+, NH_4^+$ |
| FS-5 | $F(CF_2CF_2)_nCH_2CH_2SCH_2CH_2COO^-Li^+$ | $n = 1\sim9$ |
| Cationic | | |
| FS-6 | $F(CF_2CF_2)_nCH_2CH_2SO_2NHCH_2CH_2CH_2N^+(CH_3)_3$ | <br>n=1~7 |
| FS-7 | $F(CF_2CF_2)_nCH_2CH_2SO_2NHCH_2CH_2CH_2OCH_2CH_2N^+(CH_3)_3$ | <br>n=1~7 |
| FS-8 | $F(CF_2CF_2)_nCH_2CH_2N^+(CH_3)_3Cl^-$ | $n = 1\sim9$ |
| Nonionic | | |
| FS-9 | $F(CF_2CF_2)_nCH_2CH_2O(CH_2CH_2O)_xH$ | $n = 1\sim7, x = 0\sim15$ |
| FS-10 | $F(CF_2CF_2)_nCH_2CH_2O(CH_2CH_2O)_xH$ | $n = 1\sim9, x = 0\sim25$ |
| FS-11 | $F(CF_2CF_2)_nCH_2CH_2S(CH_2CH_2O)_xH$ | $n = 1\sim9, x = 0\sim25$ |
| FS-12 | $C_6F_{13}CH_2CH_2SO_2NCH_2CH_2O(CH_2CH_2O)_xH$<br>                                 \|<br>                                 $C_3H_7$ | $x = 0\sim15$ | may be carried out at the same time. Namely, color image signals may be input into a cathode ray tube, to allow light to be emitted from the surface of the tube. Alternatively, a method in which an image signal of each of colors is successively input and light of each of colors is emitted in order, and then exposure is carried out through a film capable of cutting a color other than the emitted color, i.e., a surface successive exposure, may be used. Generally, among these methods the surface successive exposure is preferred from the viewpoint of high quality enhancement, because a cathode ray tube having a high covering power can be used.

The light-sensitive material of the present invention can preferably be used in the digital scanning exposure system using monochromatic high density light, such as a gas laser, a light-emitting diode, a semiconductor laser, a second harmonic generation light source (SHG) comprising a combination of nonlinear optical crystal with a semiconductor or a solid state laser using a semiconductor laser as an excitation light source. It is preferred to use a semiconductor laser, or a second harmonic generation light source (SHG) comprising a combination of nonlinear optical crystal with a solid state laser or a semiconductor laser, to make a system more compact and inexpensive. In particular, to design a compact and inexpensive apparatus having a longer duration of life and high stability, use of a semiconductor laser is preferable; and it is preferred that at least one of exposure light sources whould be a semiconductor laser.

When such a scanning exposure light source is used, the maximum spectral sensitivity wavelength of the light-sensitive material of the present invention can be arbitrarily set up in accordance with the wavelength of a scanning exposure light source to be used. Since oscillation wave length of a laser can be made half, using a SHG light source obtainable by a combination of a nonlinear optical crystal with a semiconductor laser or a solid state laser using a semiconductor as an excitation light source, blue light and green light can be obtained. Accordingly, it is possible to have the spectral sensitivity maximum of a photographic material in normal three wavelength regions of blue, green and red.

The exposure time in such a scanning exposure is defined as the time necessary to expose the size of the picture element (pixel) with the density of the picture element being 400 dip, and preferred exposure time is $10^{-4}$ sec or less and more preferably $10^{-6}$ sec or less.

The scanning exposure system which can preferably be used for the present invention is described in detail in the patent publications as shown in the above table.

With respect to the processing method of the photographic material of the present invention, processing materials and processing methods, as disclosed in JP-A-2-207250, from page 26, right under column, line 1 to page 34, right upper column, line 9, and JP-A-4-97355, from page 5, left upper column, line 17 to page 18, right under column, line 20, can be preferably applied. Further, as preservatives which are used in the developing solution, compounds described in the patent publications as shown in the above table are preferably used.

The present invention is preferably applied to a light-sensitive material having rapid processing suitability.

The term "color developing time" as used herein refers to a period of time required from the beginning of dipping a light-sensitive material into a color developing solution until the light-sensitive material is dipped into a blix solution in the subsequent processing step. In the case where a processing is carried out using, for example, an autoprocessor, the color developing time is the sum total of a time in which a light-sensitive material has been dipped in a color developing solution (so-called "time in the solution") and a time in which the light-sensitive material has been conveyed in air toward a bleach-fixing bath in the step subsequent to color development (so-called "time in the air"). Likewise, the term "blix time" as used herein refers to a period of time required from the beginning of dipping a light-sensitive material into a blix solution until the light-sensitive material is dipped into a washing bath or a stabilizing bath in the subsequent processing step. Further, the term "washing or stabilizing time" as used herein refers to a period of time required from the beginning of dipping a light-sensitive material into a washing solution or a stabilizing solution until the end of the dipping toward a drying step (so-called "time in the solution").

In the present invention, the color-developing time is preferably 60 sec or less, more preferably from 50 sec to 6 sec, further preferably from 30 sec to 6 sec. Likewise, the blix time is preferably 60 sec or less, more preferably from 50 sec to 6 sec, further preferably from 30 sec to 6 sec. Further, the washing or stabilizing time is preferably 150 sec or less, more preferably from 130 sec to 6 sec.

Examples of a development method applicable to the photographic material of the present invention after exposure, include a conventional wet system, such as a development method using a developing solution containing an alkali agent and a developing agent, and a development method wherein a developing agent is incorporated in the photographic material and an activator solution, e.g., a developing agent-free alkaline solution is employed for the development, as well as a heat development system using no processing solution. In particular, the activator method using a developing agent-free alkaline solution is preferred over the other methods, because the processing solution contains no developing agent, thereby it enables easy management and handling of the processing solution and reduction in waste disposal load to make for environmental preservation.

The preferable developing agents or their precursors incorporated in the photographic materials in the case of adopting the activator method include the hydrazine compounds described in, for example, JP-A-8-234388, JP-A-9-152686, JP-A-9-152693, JP-A-9-211814 and JP-A-9-160193.

Further, the processing method in which the photographic material reduced in the amount of silver to be applied undergoes the image amplification processing using hydrogen peroxide (intensification processing), can be employed preferably. In particular, it is preferably to apply this processing method to the activator method. Specifically, the image-forming methods utilizing an activator solution containing hydrogen peroxide, as disclosed in JP-A-8-297354 and JP-A-9-152695 can be preferably used.

Although the processing with an activator solution is generally followed by a desilvering step in the activator method, the desilvering step can be omitted in the case of applying the image amplification processing method to photographic materials having reduced silver coverage. In such a case, washing or stabilization processing can follow the processing with an activator solution to result in simplification of the processing process. On the other hand, when the system of reading the image information from photographic materials by means of a scanner or the like is employed, the processing form requiring no desilvering step can be applied, even if the photographic materials are those having high silver coverage, such as photographic materials for shooting.

The activator solution, desilvering solution (bleaching/fixing solution), washing solution and stabilizer for use in the present invention can contain known ingredients and can be used in conventional manners. Preferably, those described in *Research Disclosure*, Item 36544, pp. 536–541 (September 1994), and JP-A-8-234388 can be used in the present invention.

It is preferred to use a band stop filter, as described in U.S. Pat. No. 4,880,726, when the photographic material of the present invention is subjected to exposure with a printer. Color mixing of light can be excluded and color reproducibility is remarkably improved by the above means.

In the present invention, a yellow microdot pattern may be previously formed by pre-exposure before giving an image information, to thereby perform a copy restraint, as described in European Patent Nos. 0789270 A1 and 0789480 A1.

According to the novel pyrrolotriazole compound of the present invention, a dye having excellent hue and light fastness can be obtained. Particularly, the pyrrolotriazole compound of the present invention is useful as a dye-forming compound. When the pyrrolotriazole compound of the present invention is used as a cyan coupler for a silver halide color photographic light-sensitive material, such excellent effects are exhibited that color-forming property is high, the dye image obtained is excellent in light fastness, and a cyan hue with no color contamination can be obtained, without dependency on the cyan density. The silver halide color photographic light-sensitive material of the present invention, which contains the above-described compounds, is excellent in both color reproduction and light fastness, and moreover it has high illumination intensity exposure suitability.

The present invention will be described in more detail based on the examples given below, but the present invention is not meant to be limited by these examples.

EXAMPLES

Examples 1

Synthesis of Exemplified Compound

Exemplified Compound (2) was synthesized according to the following relation scheme:

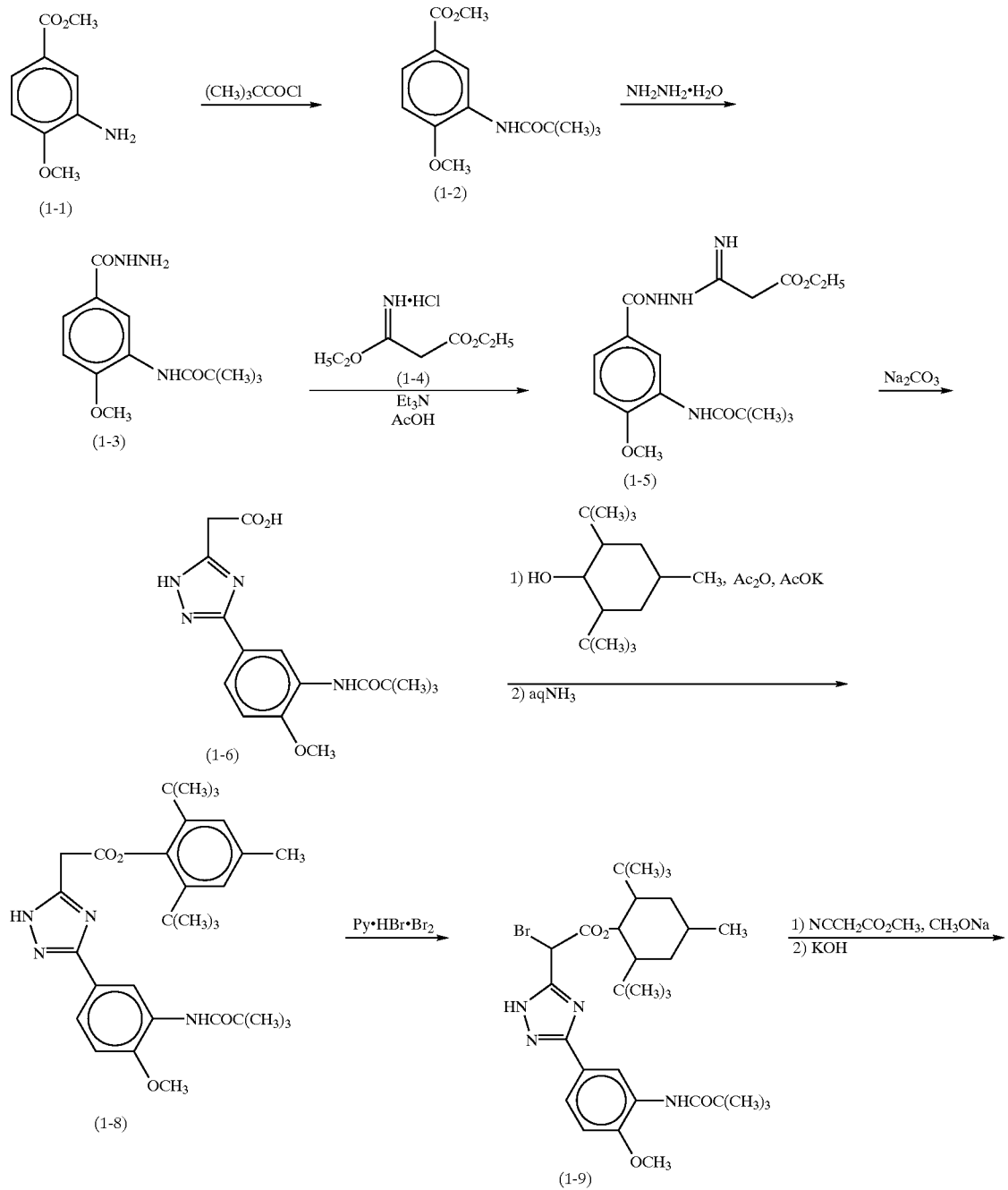

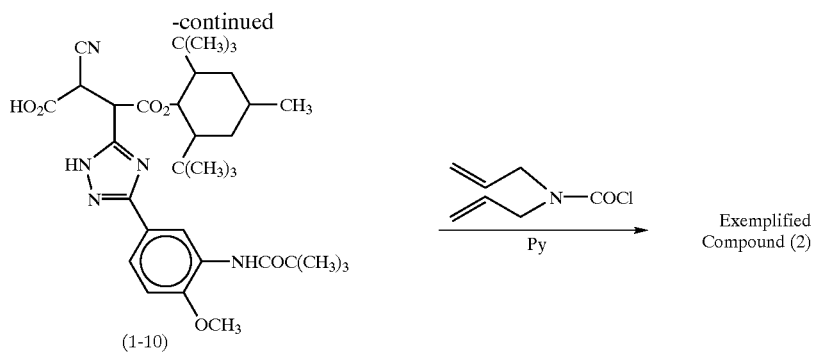

Synthesis of Intermediate (I-2)

A solution of 427 g of Compound (I-1) dissolved in 1 liter of N,N-dimethylacetamide was cooled on an ice bath with the internal temperature kept at 20° C. or less, and 293 g of pivaloyl chloride was added, dropwise, thereto, while stirring to react them. Thereafter, the ice bath was removed and stirring was continued in the reaction mixture for 3 hours at a room temperature. After the completion of reaction, 1 liter of water was added to the reaction liquid while stirring, and then precipitated crystals were collected by filtration. The crystals were washed with water and dried. As a result, 617 g (yield 99%) of the objective Intermediate (I-2) was obtained, as a white crystal.

Synthesis of Intermediate (I-3)

To a mixture of 617 g of the foregoing Intermediate (I-2) suspended in 1.8 liters of isopropyl alcohol, 565 ml of hydrazine monohydrate was added and heat-refluxed on a steam bath. Following reacting for 9 hours, the reaction mixture was cooled to 50° C. and then 2 liters of water was added and brought to a room temperature. Precipitated crystals were collected by filtration. The crystals were washed with water and dried. As a result, 586 g (yield 95%) of the objective Intermediate (I-3) was obtained, as a white crystal.

Synthesis of Intermediate (I-5)

To a mixture of 281 g of Compound (I-4) suspended in 1.6 liters of acetonitrile, 210 ml of triethylamine was added while stirring at a room temperature. Following stirring for 30 minutes, 318 g of the foregoing Intermediate (I-3) and 36 ml of acetic acid were added in this order to react them. After reacting for 10 hours, 3 liters of water was added and stirring was continued. Precipitated crystals were collected by filtration. The crystals were washed with water and dried. As a result, 324 g (yield 71%) of the objective Intermediate (I-5) was obtained, as a white crystal.

Synthesis of Intermediate (I-6)

To a mixture of 324 g of the foregoing Intermediate (I-5) suspended in 2 liters of water, 182 g of anhydrous sodium carbonate was added and heated while stirring on a steam bath. Following reacting for 5 hours, the reaction liquid was cooled to a room temperature. The resulting reaction liquid was poured into a mixture of 500 ml of acetonitrile, 360 ml of concentrated hydrochloric acid and 500 g of ice, while stirring. Precipitated crystals were collected by filtration. The crystals were washed with water and dried. As a result, 272 g (yield 95%) of the objective Intermediate (I-6) was obtained, as a white crystal.

Synthesis of Intermediate (I-8)

To a mixture of 186 g of Compound (I-7) and 272 g of the foregoing Intermediate (I-6) suspended in 1.4 liter of ethyl acetate, 161 g of potassium acetate and 387 ml of anhydrous acetic acid were added in this order and stirred at 45° C. for 3 hours on a steam bath to react them. Thereafter, the reaction mixture was cooled on an ice bath and then 1 liter of water was added. Following stirring for 1 hour while cooling on an ice bath, precipitated crystals were collected by filtration. The crystals were washed with water. Crystals thus obtained were suspended in 1.5 liters of methanol and then 400 ml of a 25% aqueous ammonia was added. The resulting mixture was stirred at 40° C. for 3 hours on a hot water bath and then cooled on an ice bath and subjected to neutralization with dilute hydrochloric acid. Precipitated crystals were collected by filtration. The crystals were washed with water and dried. As a result, 291 g (yield 66%) of the objective Intermediate (I-8) was obtained, as a white crystal.

Synthesis of Intermediate (I-9)

To a mixture of 265 g of the foregoing Intermediate (I-8) suspended in 2.5 liters of ethyl acetate, 173 g of hydrobromic acid pyridinium perbromide was added and heated while stirring at 50° C. on a hot water bath. Following reacting for 7 hours, the reaction mixture was cooled and 1 liter of water was added thereto. The organic layer was separated and washed with water and then a saturated brine. Thereafter, the organic layer was dried with anhydrous magnesium sulfate and a solvent thereof was removed by distillation. As a result, 303 g (yield 100%) of the objective Intermediate (I-9) was obtained, as a white crystal.

Synthesis of Intermediate (I-10)

A solution of 17.6 ml of sodium methoxide 28% methanol solution dissolved in 80 ml of N,N-dimethylacetamide was cooled on an ice bath with the internal temperature kept at 10° C. or less, and 7.9 ml of methyl cyanoacetate was added, dropwise, thereto. Following stirring for 30 minutes under the same condition, 22.1 g of the foregoing Intermediate (I-9) was added little by little. After the completion of addition, stirring was continued for 30 minutes and then an aqueous solution of 6 g of potassium hydroxide dissolved in 20 ml of water was added thereto. The reaction mixture was stirred for 4 hours at 50° C. on a hot water bath. After the completion of reaction, the reaction liquid was poured into an ice water containing 18 ml of conc. hydrochloric acid. The reaction liquid was extracted with ethyl acetate and the thus-extracted organic layer was washed with water and then a saturated brine. The organic layer was dried with anhydrous magnesium sulfate and a solvent thereof was removed by distillation. As a result, 22 g (yield 99%) of the objective Intermediate (I-10) was obtained, as a crystal.

Synthesis of Exemplified Compound (2)

To a solution of 22 g of the foregoing Intermediate (I-10) dissolved in 60 ml of N,N-dimethylacetoamide, 12.5 g of diallylcarbamoyl chloride and 15 ml of pyridine were added in this order and they were reacted for 10 hours at 40° C. on a hot water bath. After the completion of reaction, the reaction mixture was poured into a dilute hydrochloric acid. Precipitated crystals were collected by filtration. The crystals were washed with water and dried. These coarse crystals were recrystalized from 200 ml of acetonitrile. The thus-precipitated crystals were collected by filtration. The crystals were washed with acetonitrile and then dried. As a result, 15 g (yield 58%) of the objective exemplified compound (2) was obtained, as a white crystal.

The chemical structure of the compounds thus obtained was identified by $^1$H NMR and mass spectrum.

$^1$H-NMR (300 MHz, CDCl$_3$) δ 0.91 (18H, S), 1.08 (3H, d), 1.1–1.8 (7H, m), 1.33 (9H, s), 3.94 (3H, s), 4.02 (2H, m), 4.08 (2H, m), 5.28 (4H, m), 5.90 (2H, m), 5.92 (1H, s), 6.95 (1H, d), 7.77 (1H, dd), 8.16 (1H, s), 8.98 (1H, d), 12.15 (1H, br, s) MS m/z 728 (M$^+$) Melting Point 222–233° C.

Other exemplified compounds were synthesized in the same manner as above.

The melting points of typical exemplified compounds are shown below.

| Exemplified compound (1) | 192–200° C. |
| Exemplified compound (3) | 195–198° C. |
| Exemplified compound (4) | 180–185° C. |
| Exemplified compound (5) | 210–215° C. |
| Exemplified compound (6) | 191–195° C. |
| Exemplified compound (7) | 210–215° C. |
| Exemplified compound (8) | 215–217° C. |
| Exemplified compound (9) | 250° C. or higher |
| Exemplified compound (10) | 223–224° C. |
| Exemplified compound (12) | 216–220° C. |
| Exemplified compound (13) | 250° C. or higher |

Example 2

The surface of a paper support laminated with a polyethylene resin on both sides was subjected to corona discharge, and then provided with a gelatin subbing layer in which sodium dodecylbenzene sulfonate was incorporated. Thereon, photographic constituent layers composed of the first layer to the seventh layer were further coated, to prepare a silver halide color photographic light-sensitive material (Sample 001) having the layer structure as shown below. Coating solutions used for each of the photographic constituent layers were prepared in the following manners.

Preparation of Fifth Layer Coating Solution 190 g of a cyan coupler (ExC-2), 44 g of a cyan coupler (ExC-3), 900 g of a gelatin, 44 g of a color-image stabilizer (Cpd-1), 73 g of a color-image stabilizer (Cpd-6), 29 g of a color-image stabilizer (Cpd-7), 58 g of a color-image stabilizer (Cpd-9), 15 g of a color-image stabilizer (Cpd-10), 15 g of a color-image stabilizer (Cpd-14), 44 g of a color-image stabilizer (Cpd-15), 73 g of a color-image stabilizer (Cpd-16), 73 g of a color-image stabilizer (Cpd-17), 88 g of a color-image stabilizer (Cpd-18), and 88 g of a color-image stabilizer (Cpd-19) were dissolved in 219 g of a solvent (Solv-5), 146 g of a solvent (Solv-8), 73 g of a solvent (Solv-9), and 250 ml of ethyl acetate, and the resulting solution was emulsified and dispersed in 6500 g of a 10% aqueous gelatin solution containing 200 ml of 10% sodium dodecylbenzene sulfonate, to prepare an emulsified dispersion C.

On the other hand, a silver chlorobromide emulsion C (cubes; a 1:4 mixture of a large-size emulsion C having an average grain size of 0.50 μm, and a small-size emulsion C having an average grain size of 0.41 μm (in terms of mol of silver). The deviation coefficients of the grain size distributions were 0.09 and 0.11, respectively. Each size emulsion had 0.5 mol % of silver bromide locally contained in part of the grain surface whose substrate was made up of silver chloride) was prepared.

To the large-size emulsion C of this emulsion, had been added 6.0×10$^{-5}$ mol, per mol of silver, of each of red-sensitive sensitizing dyes G and H shown below, and to the small-size emulsion C of this emulsion, had been added 9.0×10$^{-5}$ mol, per mol of silver, of each of red-sensitive sensitizing dyes G and H shown below. Further, the chemical ripening of this emulsion was carried out optimally with a sulfur sensitizer and a gold sensitizer being added.

The above emulsified dispersion C and this silver chlorobromide emulsion C were mixed and dissolved, and a fifth-layer coating solution was prepared so that it would have the composition shown below. The coating amount of the emulsion is in terms of silver.

The coating solutions for the first layer to the fourth layer and for the sixth layer to the seventh layer were prepared in the similar manner as that for the fifth-layer coating solution. As the gelatin hardener for each layer, 1-oxy-3,5-dichloro-s-triazine sodium salt was used.

Further, to each layer, were added Ab-1, Ab-2, Ab-3, and Ab-4, so that the total amounts would be 15.0 mg/m$^2$, 60.0 mg/m$^2$, 5.0 mg/m$^2$, and 10.0 mg/m$^2$, respectively.

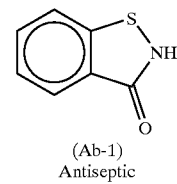

(Ab-1)
Antiseptic

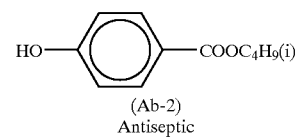

(Ab-2)
Antiseptic

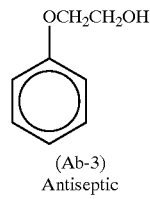

(Ab-3)
Antiseptic

Blue-sensitive Emulsion Layer

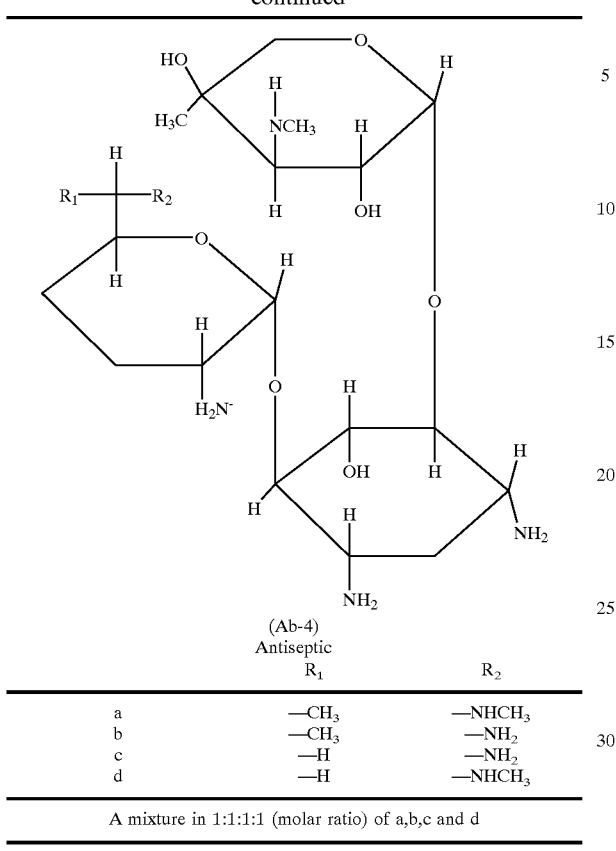

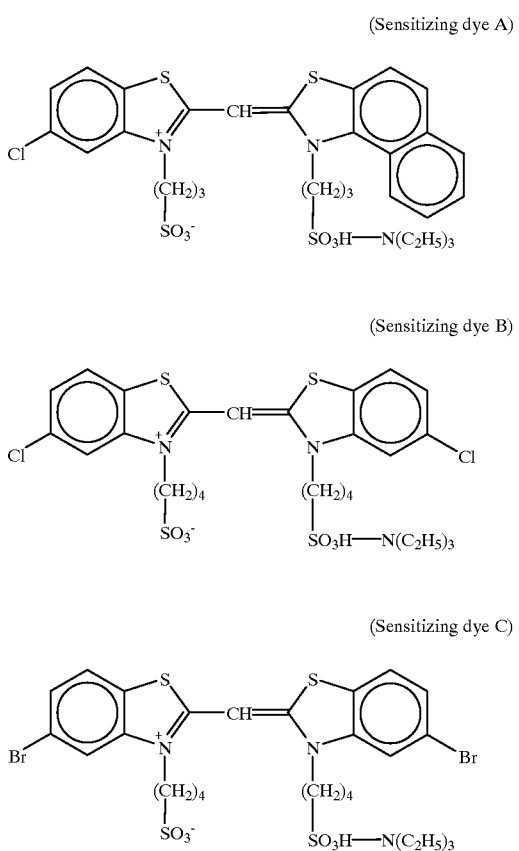

(Ab-4)
Antiseptic

| | $R_1$ | $R_2$ |
|---|---|---|
| a | —$CH_3$ | —$NHCH_3$ |
| b | —$CH_3$ | —$NH_2$ |
| c | —H | —$NH_2$ |
| d | —H | —$NHCH_3$ |

A mixture in 1:1:1:1 (molar ratio) of a,b,c and d

For the silver chlorobromide emulsion of the respective light-sensitive emulsion layer, the following spectral sensitizing dyes were used.

(The sensitizing dyes A, B, and C were added to the large-size emulsion in an amount of $1.4 \times 10^{-4}$ mol, respectively per mol of silver halide, and to the small-size emulsion in an amount of $1.7 \times 10^{-4}$ mol, respectively per mol of silver halide.)

Green-Sensitive Emulsion Layer

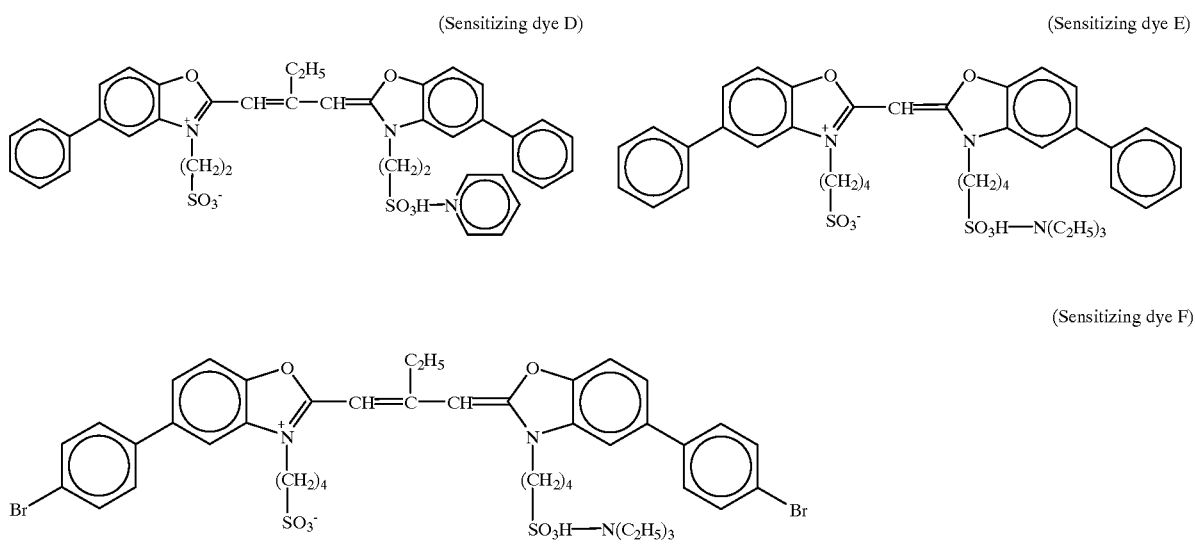

(The sensitizing dye D was added to the large-size emulsion in an amount of $3.0 \times 10^{-4}$ mol, and to the small-size emulsion in an amount of $3.6 \times 10^{-4}$ mol, per mol of the silver halide; the sensitizing dye E was added to the large-size emulsion in an amount of $4.0 \times 10^{-5}$ mol, and to the small-size emulsion in an amount of $7.0 \times 10^{-5}$ mol. per mol of the silver halide; and the sensitizing dye F was added to the large-size emulsion in an amount of $2.0 \times 10^{-4}$ mol, and to the small-size emulsion in an amount of $2.8 \times 10^{-4}$ mol, per mol of the silver halide.)

Red-Sensitive Emulsion Layer

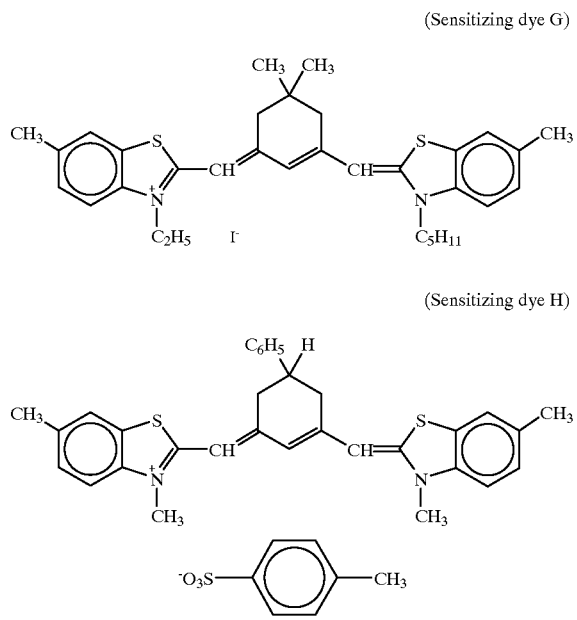

(Sensitizing dye G)

(Sensitizing dye H)

(The sensitizing dyes G, and H were added to the large-size emulsion in an amount of $6.0 \times 10^{-5}$ mol, respectively per mol of silver halide, and to the small-size emulsion in an amount of $9.0 \times 10^{-5}$ mol, respectively per mol of silver halide.)

Further, the following compound I was added to the red-sensitive emulsion layer in an amount of $2.6 \times 10^{-3}$ mol per mol of the silver halide.

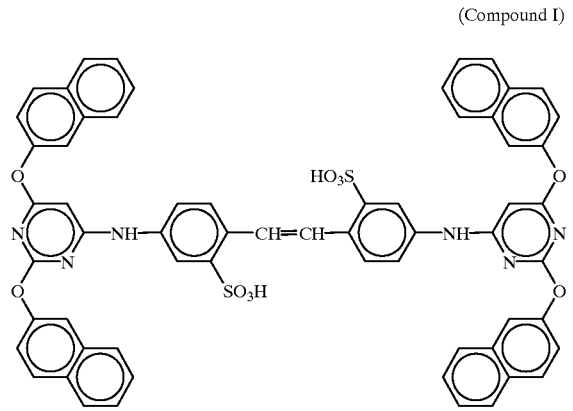

(Compound I)

Further, to the blue-sensitive emulsion layer, the green-sensitive emulsion layer, and the red-sensitive emulsion layer, was added 1-(3-methylureidophenyl)-5-mercaptotetrazole in amounts of $3.3 \times 10^{-4}$ mol, $1.0 \times 10^{-3}$ mol, and $5.9 \times 10^{-4}$ mol, respectively, per mol of the silver halide.

Further, the compound was also added to the second layer, the forth layer, the sixth layer, and the seventh layer, in amounts of 0.2 mg/m², 0.2 mg/m², 0.6 mg/m², and 0.1 mg/m², respectively.

Further, to the blue-sensitive emulsion layer and the green-sensitive emulsion layer, was added 4-hydroxy-6-methyl-1,3,3a,7-tetrazaindene in amounts of $1 \times 10^{-4}$ mol and $2 \times 10^{-4}$ mol, respectively, per mol of the silver halide.

Further, to the red-sensitive emulsion layer, was added a copolymer of methacrylic acid and butyl acrylate (1:1 in weight ratio; average molecular weight, 200,000 to 400,000) in an amount of 0.05 g/m².

Further, to the second layer, the fourth layer, and the sixth layer, was added disodium catechol-3,5-disulfonate in amounts of 6 mg/m², 6 mg/m², and 18 mg/m², respectively.

Further, in order to prevent irradiation, the following dyes (coating amounts are shown in parentheses) were added to the emulsion layers.

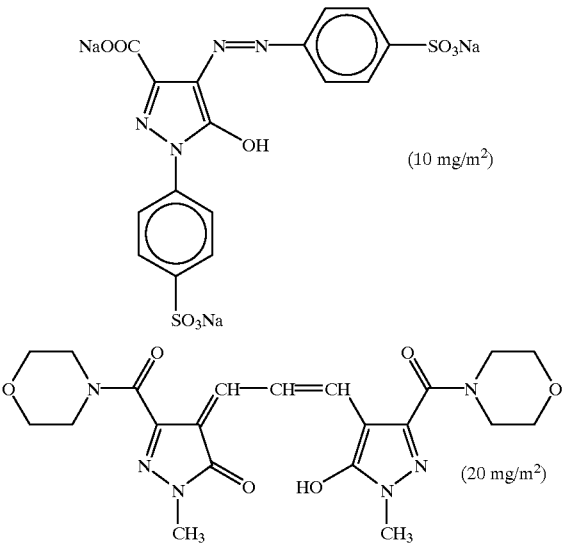

(10 mg/m²)

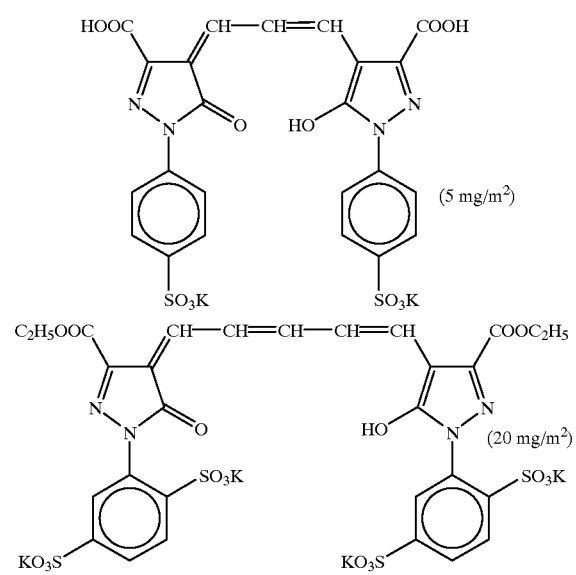

(20 mg/m²)

(5 mg/m²)

(20 mg/m²)

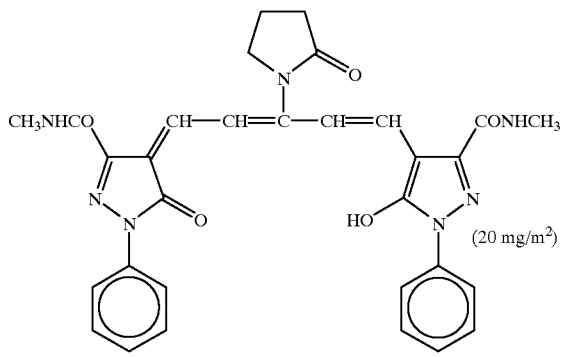
(20 mg/m²)

Layer Constitution

The composition of each layer is shown below. The numbers show coating amounts (g/m²). In the case of the silver halide emulsion, the coating amount is in terms of silver.

Support

Polyethylene Resin Laminated Paper

[The polyethylene resin on the first layer side contained a white pigment (TiO₂; content of 16 wt %, ZnO; content of 4 wt %), a fluorescent whitening agent (a mixture of 4,4'-bis(benzoxazolyl)stilbene and 4,4'-bis(5-methylbenzoxazolyl)stilbene mixed in a ratio of 8/2; content of 0.05 wt %) and a bluish dye (ultramarine)]

| First Layer (Blue-Sensitive Emulsion Layer) | |
|---|---|
| A silver chlorobromide emulsion (cubes, a 3:7 mixture of a large-size emulsion A having an average grain size of 0.72 μm, and a small-size emulsion A having an average grain size of 0.60 μm (in terms of mol of silver). The deviation coefficients of the grain size distributions were 0.08 and 0.10, respectively. Each emulsion had 0.3 mol % of silver bromide contained locally in part of the grain surface whose substrate was made up of silver chloride) | 0.26 |
| Gelatin | 1.35 |
| Yellow coupler (ExY) | 0.62 |
| Color-image stabilizer (Cpd-1) | 0.08 |
| Color-image stabilizer (Cpd-2) | 0.04 |
| Color-image stabilizer (Cpd-3) | 0.08 |
| Solvent (Solv-1) | 0.23 |
| Second Layer (Color-Mixing Inhibiting Layer) | |
| Gelatin | 0.99 |
| Color-mixing inhibitor (Cpd-4) | 0.09 |
| Color-image stabilizer (Cpd-5) | 0.018 |
| Color-image stabilizer (Cpd-6) | 0.13 |
| Color-image stabilizer (Cpd-7) | 0.01 |
| Solvent (Solv-1) | 0.06 |
| Solvent (Solv-2) | 0.22 |
| Third Layer (Green-Sensitive Emulsion Layer) | |
| A silver chlorobromide emulsion B (cubes, a 1:3 mixture of a large-size emulsion B having an average grain size of 0.45 μm, and a small-size emulsion B having an average grain size of 0.35 μm (in terms of mol of silver). The deviation coefficients of the grain size distributions were 0.10 and 0.08, respectively. Each emulsion had 0.4 mol % of silver bromide contained locally in part of the grain surface whose substrate was made up of silver chloride) | 0.14 |
| Gelatin | 1.36 |
| Magenta coupler (ExM) | 0.15 |
| Ultraviolet absorbing agent (UV-1) | 0.05 |
| Ultraviolet absorbing agent (UV-2) | 0.03 |
| Ultraviolet absorbing agent (UV-3) | 0.02 |
| Ultraviolet absorbing agent (UV-4) | 0.03 |
| Ultraviolet absorbing agent (UV-6) | 0.01 |
| Color-image stabilizer (Cpd-2) | 0.02 |
| Color-image stabilizer (Cpd-4) | 0.002 |
| Color-image stabilizer (Cpd-6) | 0.09 |
| Color-image stabilizer (Cpd-8) | 0.02 |
| Color-image stabilizer (Cpd-9) | 0.03 |
| Color-image stabilizer (Cpd-10) | 0.01 |
| Color-image stabilizer (Cpd-11) | 0.0001 |
| Solvent (Solv-3) | 0.11 |
| Solvent (Solv-4) | 0.22 |
| Solvent (Solv-5) | 0.20 |
| Fourth Layer (Color-Mixing Inhibiting Layer) | |
| Gelatin | 0.71 |
| Color-mixing inhibitor (Cpd-4) | 0.06 |
| Color-image stabilizer (Cpd-5) | 0.013 |
| Color-image stabilizer (Cpd-6) | 0.10 |
| Color-image stabilizer (Cpd-7) | 0.007 |
| Solvent (Solv-1) | 0.04 |
| Solvent (Solv-2) | 0.16 |
| Fifth Layer (Red-Sensitive Emulsion Layer) | |
| A silver chlorobromide emulsion C (cubes, a 1:4 mixture of a large-size emulsion C having an average grain size of 0.50 μm, and a small-size emulsion C having an average grain size of 0.41 μm (in terms of mol of silver). The deviation coefficients of the grain size distributions were 0.09 and 0.11, respectively. Each emulsion had 0.5 mol % of silver bromide contained locally in part of the grain surface whose substrate was made up of silver chloride) | 0.20 |
| Gelatin | 1.11 |
| Cyan coupler (ExC-2) | 0.13 |
| Cyan coupler (ExC-3) | 0.03 |
| Color-image stabilizer (Cpd-1) | 0.05 |
| Color-image stabilizer (Cpd-6) | 0.05 |
| Color-image stabilizer (Cpd-7) | 0.02 |
| Color-image stabilizer (Cpd-9) | 0.04 |
| Color-image stabilizer (Cpd-10) | 0.01 |
| Color-image stabilizer (Cpd-14) | 0.01 |
| Color-image stabilizer (Cpd-15) | 0.03 |
| Color-image stabilizer (Cpd-16) | 0.05 |
| Color-image stabilizer (Cpd-17) | 0.05 |
| Color-image stabilizer (Cpd-18) | 0.06 |
| Color-image stabilizer (Cpd-19) | 0.06 |
| Solvent (Solv-5) | 0.15 |
| Solvent (Solv-8) | 0.05 |
| Solvent (Solv-9) | 0.10 |
| Sixth Layer (Ultraviolet Absorbing Layer) | |
| Gelatin | 0.66 |
| Ultraviolet absorbing agent (UV-1) | 0.19 |
| Ultraviolet absorbing agent (UV-2) | 0.06 |
| Ultraviolet absorbing agent (UV-3) | 0.06 |
| Ultraviolet absorbing agent (UV-4) | 0.05 |
| Ultraviolet absorbing agent (UV-5) | 0.08 |
| Ultraviolet absorbing agent (UV-6) | 0.01 |
| Solvent (Solv-7) | 0.25 |
| Seventh Layer (Protective Layer) | |
| Gelatin | 1.00 |
| Acryl-modified copolymer of polyvinyl alcohol (modification degree: 17%) | 0.04 |
| Liquid paraffin | 0.02 |
| Surface-active agent (Cpd-13) | 0.01 |

(Ex Y) Yellow coupler
A mixture in 60:40 (molar ratio) of
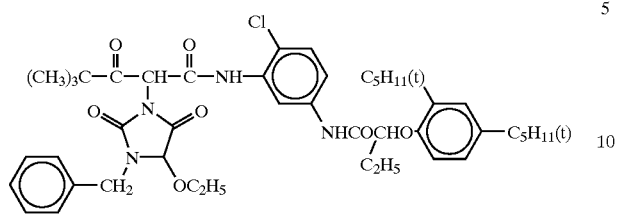
and
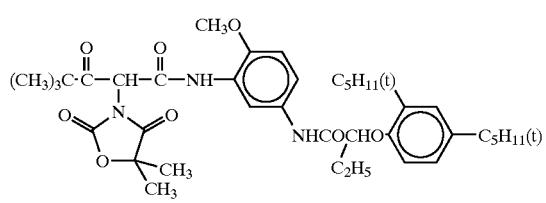
(Ex M) Magenta coupler
A mixture in 60:40 (molar ratio) of
and
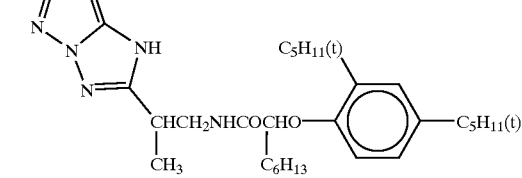
(Ex C-1) Cyan coupler
A mixture in 15:85 (molar ratio) of
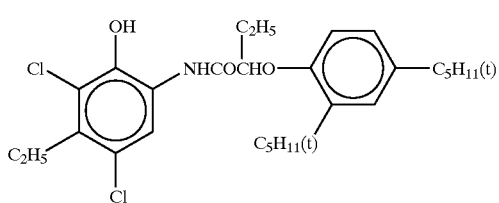
and
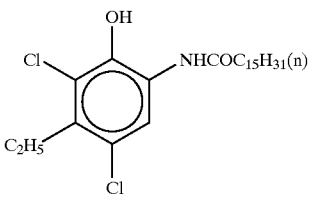
(Ex C-2) Cyan coupler
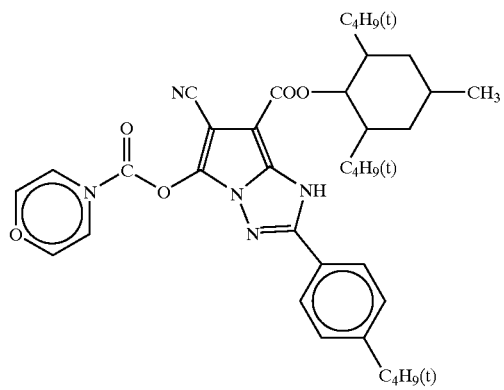
Compound (1) described in JP-A-9-189988
(Ex C-3) Cyan coupler
A mixture in 50:25:25 (molar ratio) of
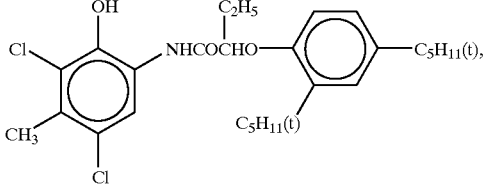
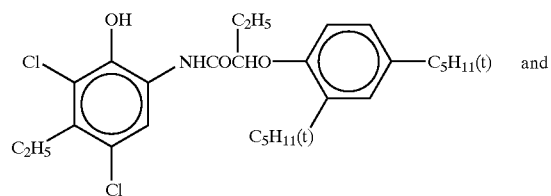 and
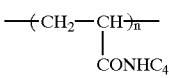
(Cpd-1) Color-image stabilizer
$-(CH_2-CH)_n-$    number-average
       |           molecular weight 60.000
  CONHC$_4$H$_9$(t)

-continued (Cpd-2) Color-image stabilizer

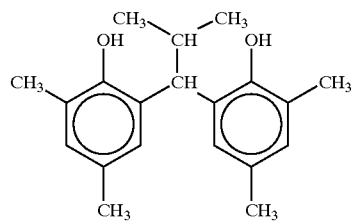

(Cpd-3) Color-image stabilizer

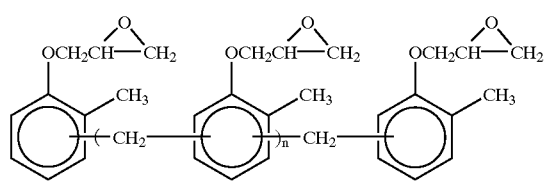

n = 7~8 (average value)

(Cpd-4) Color-mixing stabilizer

A mixture in 1:1:1 (molar ratio) of

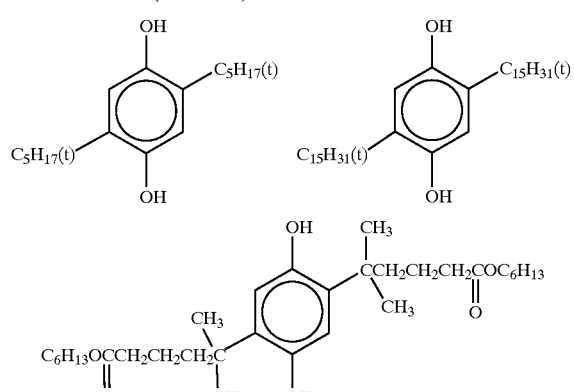

(Cpd-5) Color-image stabilizer

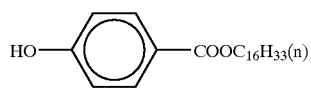

(Cpd-6) Color-image stabilizer

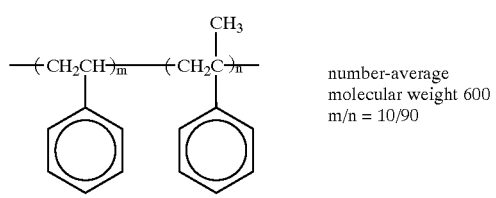

number-average molecular weight 600
m/n = 10/90

(Cpd-7) Color-image stabilizer

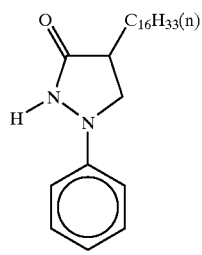

-continued (Cpd-8) Color-image stabilizer

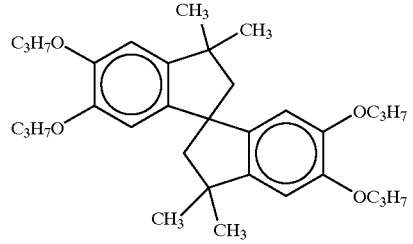

(Cpd-9) Color-image stabilizer

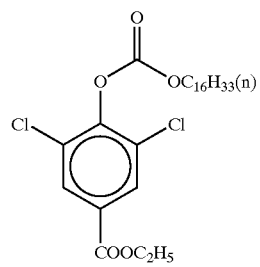

(Cpd-10) Color-image stabilizer

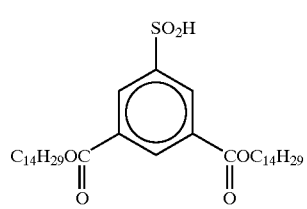

(Cpd-11) Color-image stabilizer

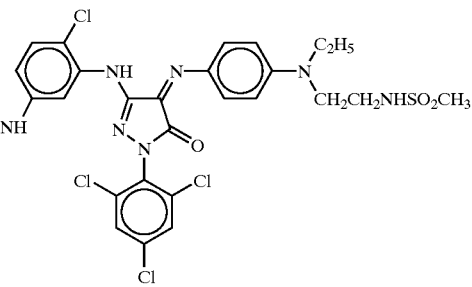

(Cpd-12) Color-image stabilizer

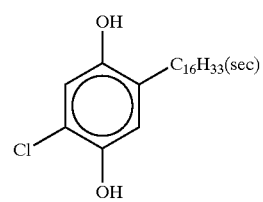

(Cpd-13) Surface-active agent

A mixture in 7:3 (molar ratio) of

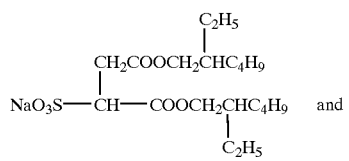

and (Cpd-14)
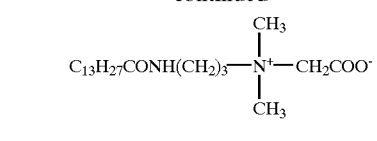
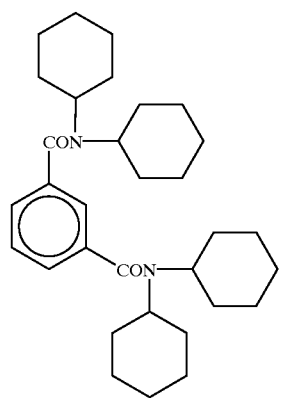
(Cpd-15)
A mixture in 1:1 (molar ratio) of
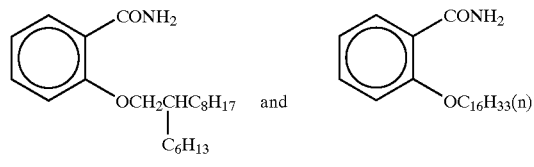 and
(Cpd-16)
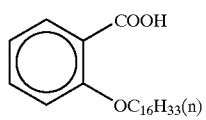
(Cpd-17)
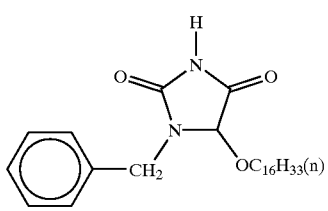
(Cpd-18)
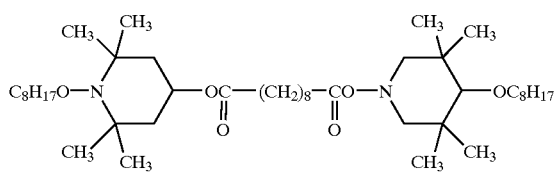
(Cpd-19)
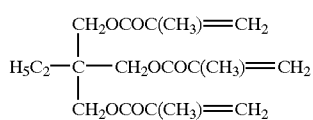
(UV-1) Ultraviolet absorbing agent
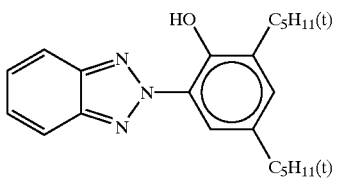
(UV-2) Ultraviolet absorbing agent
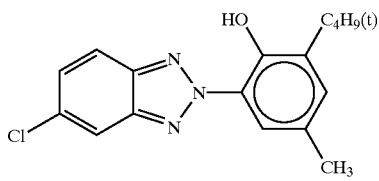
(UV-3) Ultraviolet absorbing agent
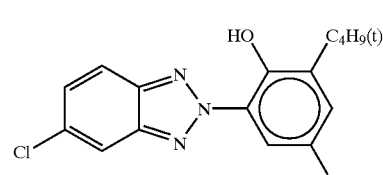
(UV-4) Ultraviolet absorbing agent
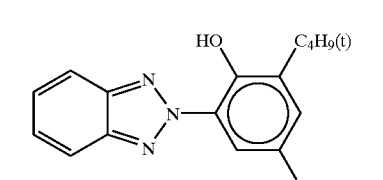
(UV-5) Ultraviolet absorbing agent
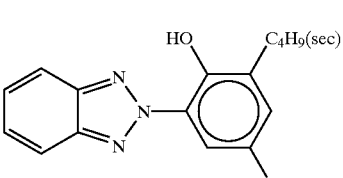
(UV-6) Ultraviolet absorbing agent
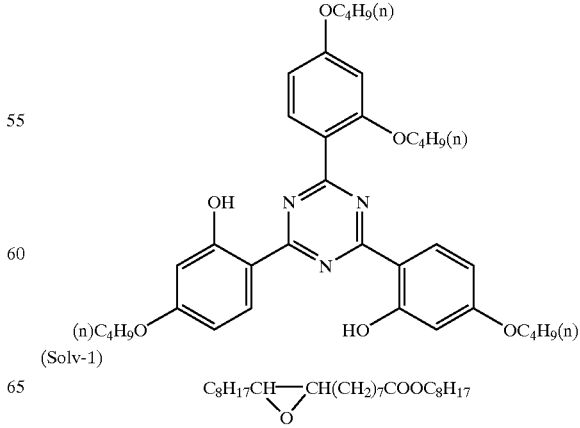
(Solv-1)
$C_8H_{17}CH\text{—}CH(CH_2)_7COOC_8H_{17}$
     \O/

-continued (Solv-2)

A mixture in 1:1 (mass ratio) of

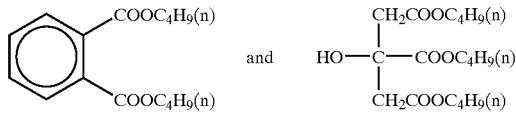 and (Solv-3)

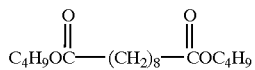

(Solv-4)

$O=P\text{-}(OC_6H_{13}(n))_3$ (Solv-5)

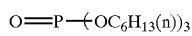

(Solv-6)

A mixture in 1:1 (mass ratio) of

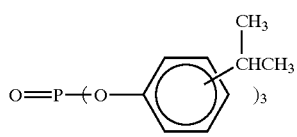

and

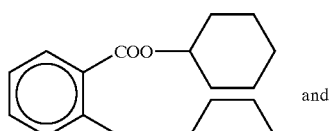

(Solv-7)

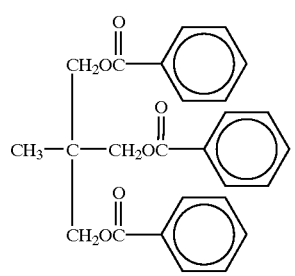

(Solv-8)

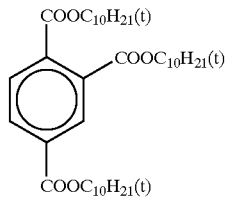

(Solv-9)

A mixture in 1:1 (mass ratio) of

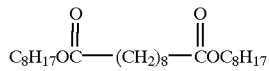 and

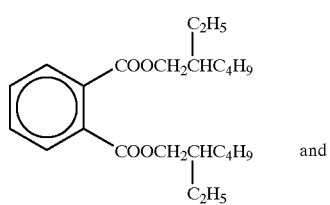

-continued

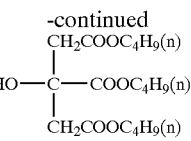

Further, the emulsifying dispersions were made in the same manner, except that the cyan coupler (ExC-2) of the emulsifying dispersion C for the fifth layer of the silver halide color photographic light-sensitive material (001) prepared as described above was altered to the compound as described in Table 2 having the same molar amount, thereby Samples (101) to (116) were prepared in the same manner as in Sample (001), except that the cyan coupler was altered like this. Further, the average particle size of the thus-prepared cyan-coupler-containing oleophilic fine-grain dispersions each were in the range of 0.10 to 0.20 μm.

The above-described light-sensitive material (001) was stored in the condition of 25° C.-55% RH, for 10 days, and then, made into a roll with a width of 127 mm; the rolled light-sensitive material was exposed to light imagewise, using a mini-lab printer processor PP1258AR, trade name, manufactured by Fuji Photo Film Co., Ltd.; and then, the continuously processing (running test) in the following processing steps was carried out, until the replenishment reached to be equal to twice the color development tank volume.

| Processing step | Temperature | Time | Replenishment rate* |
| --- | --- | --- | --- |
| Color development | 38.5° C. | 45 sec | 45 ml |
| Bleach-fixing | 38.0° C. | 45 sec | 35 ml |
| Rinse (1) | 38.0° C. | 20 sec | — |
| Rinse (2) | 38.0° C. | 20 sec | — |
| Rinse (3) | **38.0° C. | 20 sec | — |
| Rinse (4) | **38.0° C. | 30 sec | 121 ml |

*Replenishment rate per m² of the light-sensitive material to be processed.
**A rinse cleaning system RC50D, manufactured by Fuji Photo Film Co., Ltd., was installed in the rinse (3), and the rinse solution was taken out from the rinse (3) and sent to a reverse osmosis membrane module (RC50D) by using a pump. The permeated water obtained in that tank was supplied to the rinse (4), and the concentrated water was returned to the rinse (3). Pump pressure was controlled such that the water to be permeated in the reverse osmosis module would be maintained in an amount of 50 to 300 ml/min, and the rinse solution was circulated under controlled temperature for 10 hours a day. (The rinse was made in a tank countercurrent system from (1) to (4).)

The composition of each processing solution was as follows.

| | (Tank solution) | (Replenisher) |
| --- | --- | --- |
| (Color developer) | | |
| Water | 800 ml | 800 ml |
| Dimethylpolysiloxane-series surfactant (Silicone KF351A/ trade name, Shin-Etsu Chemical Co., Ltd.) | 0.1 g | 0.1 g |

-continued

|  | (Tank solution) | (Replenisher) |
|---|---|---|
| Triethanolamine | 11.6 g | 11.6 g |
| Ethylenediamine tetraacetic acid | 4.0 g | 4.0 g |
| Sodium 4,5-dihydroxybenzene-1,3-disulfonate | 0.5 g | 0.5 g |
| Potassium chloride | 10.0 g | — |
| Potassium bromide | 0.040 g | 0.010 g |
| Triazinylaminostilbene-series fluorescent whitening agent (Hakkol FWA-SF/trade name, Showa Chemical Industry Co., Ltd.) | 2.5 g | 5.0 g |
| Sodium sulfite | 0.1 g | 0.1 g |
| Disodium-N,N-bis(sulfonatoethyl)hydroxylamine | 8.5 g | 11.1 g |
| N-ethyl-N-(β-methanesulfonamidoethyl)-3-methyl-4-amino-4-aminoaniline · 3/2 sulfuric acids · 1 hydrate | 5.0 g | 15.7 g |
| Potassium carbonate | 26.3 g | 26.3 g |
| Water to make | 1000 ml | 1000 ml |
| pH (25° C./adjusted using potassium hydroxide and sulfuric acid) | 10.15 | 12.50 |
| (Bleach-fixing solution) | | |
| Water | 800 ml | 800 ml |
| Ammonium iron (III) ethylenediaminetetraacetate | 47.0 g | 94.0 g |
| Ethylenediamine tetraacetic acid | 1.4 g | 2.8 g |
| m-Carboxymethylbenzenefulfinic acid | 8.3 g | 16.5 g |
| Nitric acid (67%) | 16.5 g | 33.0 g |
| Imidazole | 14.6 g | 29.2 g |
| Ammonium thiosulfate (750 g/l) | 107 ml | 214 ml |
| Ammonium sulfite | 16.0 g | 32.0 g |
| Potassium methbisulfite | 23.1 g | 46.2 g |
| Water to make | 1000 ml | 1000 ml |
| pH (25° C./adjusted using acetic acid and ammonia) | 6.0 | 6.0 |
| (Rinse solution) | | |
| Sodium chlorinated-isocyanurate | 0.02 g | 0.02 g |
| Deionized water (conductivity: 5 μS/cm or less) | 1000 ml | 1000 ml |
| pH | 6.5 | 6.5 |

Then, each of the samples was subjected to gradation exposure using a sensitometer (Model FWH, produced by Fuji Photo Film Co., Ltd., whose light source had a color temperature of 3,200° K.) through three color separation optical wedges for sensitometry. The exposure was performed under a condition such that the exposure time was 0.1 seconds and the amount of exposure was 250 lx·sec. The thus-exposed samples were each processed with the foregoing running processing solutions, and thereby samples, in each of which a yellow, magenta, or cyan gradation color generated, were obtained.

Evaluation of Color Reproduction

Densities of the processed samples in the area with the maximum cyan color generation were each measured using a photodensitometer: an X-rite 350 Model (produced by X-rite Company). As shown in Table 3, each of the samples according to the present invention exhibited a Dmax of 2 or more, which was sufficient color density. Then, a magenta density M(C 2.0) at the cyan color-formed portion, having a cyan density of 2.0, was measured. The less value of M(C 2.0) means the more reduction of contamination due to a magenta component in a cyan coloring portion to give an excellent hue.

Evaluation of Light Fastness

Each sample having the above-described cyan dye image was exposed to xenon rays, using a device capable of irradiating xenon rays of 100,000 lux, through an ultraviolet cut filter, having a light-transmittance of 50% at 370 nm, and a heat-cut filter, for 14 days. Densities after irradiating light in the area with a cyan density of 2.0 before irradiating light, were measured, to obtain a residual percent (%) of the density, which was adopted herein as a criterion of light fastness.

The thus-obtained results are shown in Table 2.

TABLE 2

| Sample No. | Light-sensitive material Cyan coupler No.* | Color formation of Cyan Dmax | Density of Magenta in Cyan M (C2.0) | Light fastness (residual percent (%) of density of cyan) | Remarks |
|---|---|---|---|---|---|
| 001 | ExC-2 | 2.21 | 0.65 | 78 | Comparative example |
| 101 | (1) | 2.28 | 0.45 | 89 | This invention |
| 102 | (2) | 2.26 | 0.44 | 91 | This invention |
| 103 | (3) | 2.25 | 0.43 | 90 | This invention |
| 104 | (4) | 2.20 | 0.46 | 88 | This invention |
| 105 | (5) | 2.31 | 0.44 | 90 | This invention |
| 106 | (8) | 2.18 | 0.47 | 91 | This invention |
| 107 | (9) | 2.27 | 0.45 | 90 | This invention |
| 108 | (10) | 2.30 | 0.46 | 88 | This invention |
| 109 | (13) | 2.22 | 0.46 | 89 | This invention |
| 110 | (15) | 2.25 | 0.47 | 92 | This invention |
| 111 | (16) | 2.30 | 0.45 | 87 | This invention |
| 112 | (24) | 2.24 | 0.45 | 89 | This invention |
| 113 | (25) | 2.17 | 0.44 | 90 | This invention |
| 114 | (26) | 2.26 | 0.46 | 88 | This invention |
| 115 | CC-1 | 1.02 | — | 74** | Comparative example |
| 116 | CC-2 | 2.24 | 0.66 | 77 | Comparative example |

*All samples contained ExC-3.
**The value evaluated in initial density; 1.0

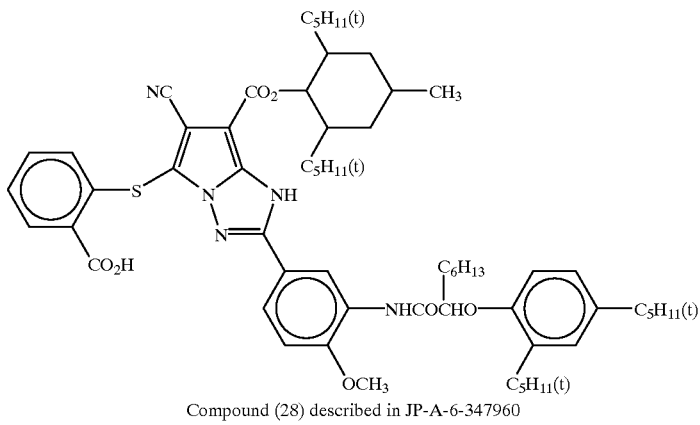

Compound (28) described in JP-A-6-347960

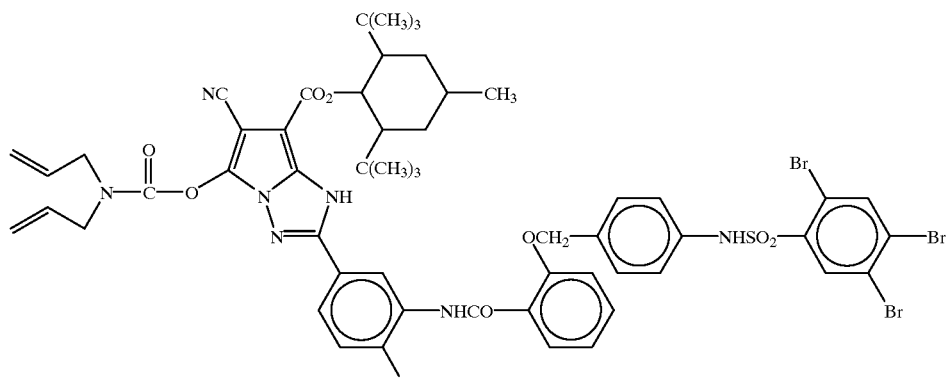

Compound (31) described in JP-A-10-198009

The results in Table 2 show that the samples obtained by using the cyan coupler of the present invention provided less magenta density in the cyan color-formed portion, and therefore gave excellent cyan hue, than did sample (001) for comparison, obtained by using a conventional cyan coupler. Further, it was also confirmed, by an organoleptic test by the naked eyes, that the samples according to the present invention provided less contamination due to magenta or yellow in the cyan color and excellent cyan hue, than did the comparative samples.

Further, from the results of fading tests owing to xenon rays, as shown in Table 2, it can be understood that the use of cyan coupler of the present invention also considerably improved light fastness.

Evaluation of the Magenta Component in each Cyan Density

The values of magenta density DM(Cy) in the areas with cyan densities of 0.5, 1.0, and 2.0, respectively, were each measured according to the equation defined below.

$$DM(Cy)=(M(Cy)-Dmin(M))/(Cy-Dmin(C))$$

Cy: Cyan density (y =0.5, 1.0, or 2.0)

M(Cy): Magenta density in the cyan color-formed portion having a cyan density of y Dmin(M): Minimum magenta density Dmin(C): Minimum cyan density The less value of DM(Cy) means the more reduction of the magenta density in the cyan color-formed portion, which is preferable. In addition, the less difference in DM(Cy) between Cy's, which were different from each other, means the more reduction of the dependency of cyan hue upon density, which is preferable.

The results that were obtained by the samples of the present Example according to the above method, are shown in Table 3.

TABLE 3

| Light-sensitive material | | Density of Magenta in each density of Cyan | | | |
|---|---|---|---|---|---|
| Sample No. | Cyan coupler No. | DM (C0.5) | DM (C1.0) | DM (C2.0) | Remarks |
| 001 | ExC-2 | 0.32 | 0.30 | 0.23 | Comparative example |
| 101 | (1) | 0.15 | 0.15 | 0.14 | This invention |
| 102 | (2) | 0.14 | 0.14 | 0.13 | This invention |
| 103 | (3) | 0.15 | 0.15 | 0.15 | This invention |
| 104 | (4) | 0.16 | 0.15 | 0.15 | This invention |
| 105 | (5) | 0.15 | 0.14 | 0.14 | This invention |
| 106 | (8) | 0.14 | 0.14 | 0.14 | This invention |
| 107 | (9) | 0.15 | 0.15 | 0.15 | This invention |
| 108 | (10) | 0.16 | 0.15 | 0.14 | This invention |
| 109 | (13) | 0.17 | 0.17 | 0.15 | This invention |

TABLE 3-continued

| Light-sensitive material | | Density of Magenta in each density of Cyan | | | |
|---|---|---|---|---|---|
| Sample No. | Cyan coupler No. | DM (C0.5) | DM (C1.0) | DM (C2.0) | Remarks |
| 110 | (15) | 0.15 | 0.15 | 0.14 | This invention |
| 111 | (16) | 0.14 | 0.14 | 0.13 | This invention |
| 112 | (24) | 0.17 | 0.17 | 0.16 | This invention |
| 113 | (25) | 0.16 | 0.16 | 0.16 | This invention |
| 114 | (26) | 0.15 | 0.15 | 0.14 | This invention |
| 115 | CC-1 | 0.31 | 0.31 | — | Comparative example |
| 116 | CC-2 | 0.33 | 0.31 | 0.24 | Comparative example |

In Table 3, the results shows that not only the values of DM(Cy) in the areas with cyan densities of 0.5, 1.0, and 2.0, respectively, but also a difference in the values of DM(Cy) between these different cyan densities, which were obtained by the samples according to the present invention, were each quite less than those of the samples for comparison. From the results, it is understood that comparative sample (116), produced by using a conventional cyan coupler, had the drawback that the less cyan density Cy was accompanied with the more-increased magenta density in the cyan color-formed area, whereas the samples according to the present invention provided excellent cyan hue regardless of the cyan density.

Example 3

Each sample was processed and evaluated in the same manner as in Example 2, except that light-sensitive materials were exposed by the following scanning exposure. Similarly to Example 2, the results showed that each of the samples produced using the cyan coupler represented by formula (I) according to the present invention, was excellent in both the hue of the resulting dye and the light fastness.

As for the scanning exposure, the scanning exposure device illustrated in FIG. 1 of JP-A-8-16238 was employed. The light sources used were a light of 688 nm (R light), from a certain semiconductor laser; and a light of 532 nm (G light) and a light of 473 nm (B light), each obtained by a certain semiconductor laser combined with SHG. The quantity of the R light was modulated using an external modulator. Scanning exposure was conducted such that the laser rays were applied to each sample, which was being moved in the direction vertical to the scanning direction, by the reflection to a rotary polyhedron. The scanning exposure was performed at 400 dpi, and the average exposure time was $8 \times 10^{-8}$ seconds per pixel. Using a Peltier device, the temperatures of the semiconductor lasers each were kept constant, to prevent temperature-dependent fluctuation of the quantity of light from each laser.

Example 4

Light-sensitive material samples 001', and 101' to 116', were each prepared in the same manner as samples 001, and 101 to 116, of Example 2, except that the support was replaced by a support of polyethyleneterephthalate (the thickness of the support, 250 μm) mixed with barium sulfate, and in addition, that the protective layer (seventh layer) was changed as described below. From the results of the same evaluation as in Example 2, it was found that similar to Example 2, samples 101' to 114' according to the present invention each excelled in both color reproduction and light fastness, compared with the comparative samples 001', 115', and 116'. Further, it was found that, also when these samples were exposed in the same manner as in Example 3 at the time of preparation thereof, the samples according to the present invention similarly excelled in both color reproduction and light fastness.

Further, at the same time as the preparation of the foregoing modified samples, other light-sensitive material samples were prepared in the same manner as in Example 2, except that the same support as in Example 2 was used, and only the protective layer (seventh layer) was changed as described below. The same evaluation as in Examples 2 and 3 was conducted, and almost the same results as described above were obtained.

| Seventh Layer (Protective layer) | (Coating Amount g/m²) |
|---|---|
| Gelatin | 1.00 |
| Acryl-modified copolymer of polyvinyl alcohol (modification degree 17%) | 0.04 |
| Liquid Paraffin | 0.02 |
| Surface-Active Agent (Cpd-13) | 0.01 |
| Surface-Active Agent (Exemplified compound FS-5) | 0.01 |

Example 5

Five kinds of samples were prepared in the same manner as Sample 106 in Example 1 of JP-A-11-282106, except that the cyan coupler (EXC) was replaced by the cyan coupler (1), (2), (3), (4), or (5) of the present invention, in an equimolar amount, respectively. These samples were each exposed and processed for development in the same manner as in Example 1 of JP-A-11-282106. From the results of evaluation, it was confirmed that each of the samples containing the cyan coupler of the present invention also exhibited effects of the present invention (particularly improvement in both color-forming property and color reproduction).

Further, at the same time as the preparation of the foregoing five kinds of samples and Sample 106 in Example 1 of JP-A-11-282106, the similar samples as the above-described samples, except that the surface-active agent (Cpd-12) in the sixth layer (protective layer) was replaced by the Exemplified compound (FS-5), or alternatively the Exemplified compound (FS-3), in the same weight amount, respectively, were each prepared. Similarly, these samples were exposed and processed in the same manner as Sample 106 in Example 1 of JP-A-11-282106. From the results of evaluation, it was confirmed that the samples produced by using the coupler of the present invention each also exhibited effects of the present invention (particularly improvement in both color-forming property and color reproduction).

Having described our invention as related to the present embodiments, it is our intention that the invention not be limited by any of the details of the description, unless otherwise specified, but rather be construed broadly within its spirit and scope as set out in the accompanying claims.

What we claim is:

1. A silver halide color photographic light-sensitive material comprising a cyan coupler represented by the following formula (I):

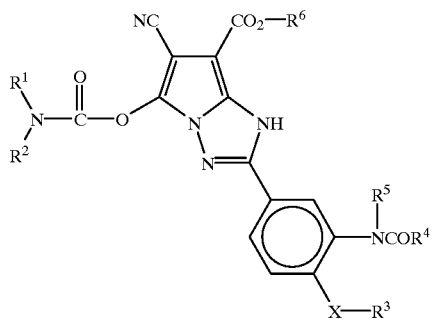

formula (I)

wherein
R¹ and R² each independently represent an alkyl group, a cycloalkyl group, an alkenyl group, an aryl group, or a heterocyclic group, provided that R¹ and R² may combine with each other to form a 5- or 6-membered nitrogen-containing heterocycle;

R³ represents an alkyl group, a cycloalkyl group, an alkenyl group, an aryl group, or a heterocyclic group;

R⁴ represents an alkyl group, a cycloalkyl group, an alkenyl group, an alkoxy group, or an amino group;

R⁵ represents a hydrogen atom, an alkyl group, or an aryl group;

R⁶ represents an alkyl group, a cycloalkyl group, or an alkenyl group; and

X represents an oxygen atom, or a sulfur atom.

2. The silver halide color photographic light-sensitive material as claimed in claim 1, wherein, in formula (I), R³ represents a substituted or unsubstituted alkyl group.

3. The silver halide color photographic light-sensitive material as claimed in claim 1, wherein, in formula (I), R⁴ represents an alkyl group or a cycloalkyl group.

4. The silver halide color photographic light-sensitive material as claimed in claim 1, wherein, in formula (I), R⁴ represents a tertiary unsubstituted alkyl group.

5. The silver halide color photographic light-sensitive material as claimed in claim 1, wherein, in formula (I), R⁶ represents a group represented by the following formula (II):

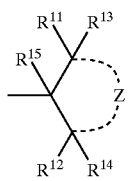

wherein, in formula (II),
R¹¹ and R¹² each independently represent an alkyl group, a cycloalkyl group, or an alkenyl group;

R¹³, R¹⁴ and R¹⁵ each independently represent a hydrogen atom, an alkyl group, a cycloalkyl group, or an alkenyl group; and Z represents carbon atoms necessary to form a 5- to 8-membered ring, which ring may be substituted, and which ring may be a saturated ring or an unsaturated ring.

6. The silver halide color photographic light-sensitive material as claimed in claim 1, wherein the cyan coupler is contained in a red-sensitive silver halide emulsion layer.

7. The silver halide color photographic light-sensitive material as claimed in claim 1,
wherein the cyan coupler is contained in an amount of 1×10⁻³ mol to 1 mol, per mol of the silver halide in the same layer.

8. The silver halide color photographic light-sensitive material as claimed in claim 1, which comprises a silver chloride or silver chlorobromide emulsion having a silver chloride content of 95 mol % or more.

9. The silver halide color photographic light-sensitive material as claimed in claim 1, which comprises a fluorine-containing surfactant.

10. A pyrrolotriazole compound represented by the following formula (I):

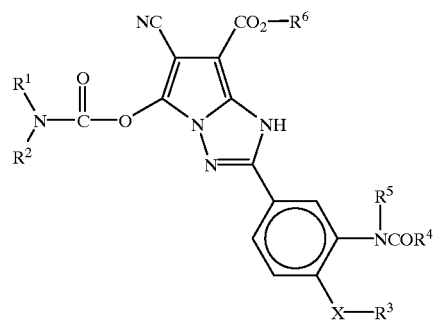

formula (I)

wherein
R¹ and R² each independently represent an alkyl group, a cycloalkyl group, an alkenyl group, an aryl group, or a heterocyclic group, provided that R¹ and R² may combine with each other to form a 5- or 6-membered nitrogen-containing heterocycle;

R³ represents an alkyl group, a cycloalkyl group, an alkenyl group, an aryl group, or a heterocyclic group;

R⁴ represents an alkyl group, a cycloalkyl group, an alkenyl group, an alkoxy group, or an amino group;

R⁵ represents a hydrogen atom, an alkyl group, or an aryl group;

R⁶ represents an alkyl group, a cycloalkyl group, or an alkenyl group; and

X represents an oxygen atom, or a sulfur atom.

11. The pyrrolotriazole compound as claimed in claim 10, wherein, in formula (I), R³ represents a substituted or unsubstituted alkyl group.

12. The pyrrolotriazole compound as claimed in claim 10, wherein, in formula (I), R⁴ represents an alkyl group or a cycloalkyl group.

13. The pyrrolotriazole compound as claimed in claim 10, wherein, in formula (I), R⁴ represents a tertiary unsubstituted alkyl group.

14. The pyrrolotriazole compound as claimed in claim 10, wherein, in formula (I), R⁶ represents a group represented by the following formula (II):

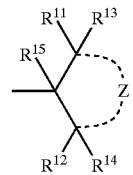

wherein, in formula (II),
R¹¹ and R¹² each independently represent an alkyl group, a cycloalkyl group, or an alkenyl group;

R¹³, R¹⁴ and R¹⁵ each independently represent a hydrogen atom, an alkyl group, a cycloalkyl group, or an alkenyl group; and Z represents carbon atoms necessary to form a 5- to 8-membered ring, which ring may be substituted, and which ring may be a saturated ring or an unsaturated ring.

15. A dye-forming material comprising the pyrrolotriazole compound as claimed in claim 10.

16. An image-forming composition comprising the dye-forming material as claimed in claim 15.

* * * * *